US008349769B2

(12) United States Patent
Wurms et al.

(10) Patent No.: US 8,349,769 B2
(45) Date of Patent: Jan. 8, 2013

(54) FUNGICIDAL COMPOSITIONS

(75) Inventors: Kirstin Verity Wurms, Hamilton (NZ); Annette Ah Chee, Hamilton (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 1143 days.

(21) Appl. No.: 11/631,974

(22) PCT Filed: Jul. 11, 2005

(86) PCT No.: PCT/NZ2005/000167
§ 371 (c)(1),
(2), (4) Date: Nov. 2, 2007

(87) PCT Pub. No.: WO2006/006878
PCT Pub. Date: Jan. 19, 2006

(65) Prior Publication Data
US 2008/0233202 A1   Sep. 25, 2008

(30) Foreign Application Priority Data
Jul. 9, 2004   (NZ) .................................. 534007

(51) Int. Cl.
*A01N 65/00*   (2009.01)
(52) U.S. Cl. ....................................................... 504/189
(58) Field of Classification Search ................... 504/189
See application file for complete search history.

(56) References Cited

U.S. PATENT DOCUMENTS

| | | | |
|---|---|---|---|
| 3,947,589 A | 3/1976 | Misato et al. | |
| 4,404,040 A | 9/1983 | Wang | |
| 4,891,385 A | 1/1990 | Synek | |
| 5,035,741 A | 7/1991 | Puritch et al. | |
| 5,093,124 A | 3/1992 | Kulenkampff | |
| 5,098,468 A | 3/1992 | Puritch et al. | |
| 5,208,257 A | 5/1993 | Kabara | |
| 5,435,992 A | 7/1995 | Audegond et al. | |
| 6,071,961 A | 6/2000 | Wider | |
| 6,103,768 A | 8/2000 | Savage et al. | |
| 2003/0206882 A1 | 11/2003 | Richter et al. | |

FOREIGN PATENT DOCUMENTS

| | | | |
|---|---|---|---|
| AU | 3253984 | | 3/1985 |
| CZ | 282052 | * | 11/1994 |
| CZ | 282052 B6 | | 5/1997 |
| DE | 10129855 A1 | | 1/2003 |
| JP | 53047532 A2 | | 4/1978 |
| JP | 02-124806 A | | 5/1990 |
| JP | 2002/293709 | | 10/2002 |
| WO | WO90/09110 | | 8/1990 |
| WO | WO 96/22020 | | 7/1996 |
| WO | WO 96/28022 | | 9/1996 |
| WO | WO 98/04157 | | 2/1998 |
| WO | WO 00/27195 | | 5/2000 |
| WO | WO01/49296 | | 7/2001 |
| WO | WO03/000053 | | 1/2003 |
| WO | WO 2004/039820 | * | 5/2004 |

OTHER PUBLICATIONS

Heimlich "Omega Nutrition" 1991, 2 pages http://www.omeganutrition.com/articles-other-agoodfat.php.*
Bitman "Status Report on the Alteration of Fatty Acid and Sterol Composition in Lipids in Meat, Milk, and Eggs" Fat Content and Composition of Animal Products : PR National Academy of Sciences Washington : 1976;():200-237.*
Cornell University Plant Disease Diagnostic Clinic "Botrytis blight factsheet" Available on Jul. 1999 at http://plantclinic.cornell.edu/FactSheets/botrytis/botrytis_blight.htm, 3 pages.*
Evans "Antioxidant Properties of Vegetable Lecithin" Industrial and Engineering Chemistry, vol. 27, No. 3, p. 329-331.*
Bringe et al. "Emulsifying Properties of Low-fat, Low-cholesterol Egg Yolk Prepared by Supercritical CO2 Extraction" vol. 61, No. 1, 1996-Journal of Food Science, pp. 19-23.*
W. Bettiol, Crop Protection, vol. 18, No. 8, 1999, pp. 489-492, Effectiveness of cow's milk against zucchini squash powdery . . . .
Bettiol. "Effectiveness of Cow's Milk Against Zucchini Squash Powdery Mildew (*Sphaerotheca fuliginea*) in Greenhouse Conditions." Crop Protection vol. 18 (1999) pp. 489-492.
Bruer et al. "Organic Control of Powdery Mildew without Sulphur." The Australian Grapegrower & Winemaker vol. 452, (2001) p. 22.
Cheah et al. "Screening of Plant Extracts for Control of Powdery Mildew." Proceedings of the 48th NZ Plant Protection Conference, (1995), pp. 340-342.
Fenigstein et al. "Effects of Five Vegetable Oils on the Sweet Potato Whitefly *Bemisia tabaci*." Phytoparasitics, vol. 29, No. 3, (2001), pp. 197-206.
McGrath et al. "Evaluation of Biocompatible Products for Managing Cucurbit Powdery Mildew." Crop Protection, vol. 18 (1999), pp. 471-478.
Kabara et al. "Antimicrobial Agents Derived from Fatty Acids." Journal of the American Oil Chemists' Society, vol. 61, No. 2, (1984) pp. 397-403.
Kabara et al. Fatty Acids and Derivatives as Antimicrobial Agents—A Review—The American's Oil Chemists' Society, pp. 1-14. Chapter 1, 1978.
Ko et al. "Effects of Sunflower Oils on Tomato Powdery Mildew Caused by *Oidium neolycopersici*." Journal of Phytopathology, vol. 151, (2003), pp. 144-148.
Moran et al. "Soybean Oil as a Summer Spray for Apple: European Red Mite Control, Net $CO_2$ Assimilation and Phytotoxicity." HortScience, vol. 38, No. 2, (2003), pp. 234-238.
Nieman et al. "Influence of Trace Amounts of Fatty Acids of the Growth of Microorganisms." Bacteriological Reveiws vol. 18, (1954), pp. 147-163.
Northover et al. "Activity of Plant Oils on Diseases Caused by *Podosphaera leucotrcha*, *Venturia inaequalis*, and *Albugo occidentalis*." Plant Disease, vol. 77, No. 2 (1993) pp. 152-157.

(Continued)

*Primary Examiner* — Irene Marx
*Assistant Examiner* — Thane Underdahl
(74) *Attorney, Agent, or Firm* — Jacobson Holman PLLC

(57) ABSTRACT

The present invention relates to fungicidal compositions and particularly fungicidal compositions comprising anhydrous milk fat (AMF), soybean oil and/or coconut fat. The invention also relates to a fungicidal method employing a composition of the invention. The compositions and methods of the invention have applications in the management (prevention and control) of fungal growth in commercial and small scale crop production.

25 Claims, 12 Drawing Sheets

OTHER PUBLICATIONS

Northover et al. "Physical Modes of Action of Petroleum and Plant Oils on Powdery and Downy Mildews of Grapevines." Plant Disease, vol. 80, No. 5 (1996) pp. 544-550.

Wilson et al. "Rapid Evaluation of Plant Extracts and Essential Oils for Antifungal Activity Against *Botrytis cinerea*." Plant Disease vol. 81, (1997), pp. 204-210.

* cited by examiner

FUNGICIDAL COMPOSITIONS

This is a national stage of PCT/NZ05/000167 filed Jul. 11, 2005 and published in English.

FIELD OF THE INVENTION

The present invention relates to fungicidal compositions and particularly fungicidal compositions comprising anhydrous milk fat (AMF), soybean oil and/or coconut fat. The invention also relates to a fungicidal method employing a composition of the invention.

BACKGROUND

Powdery mildew (PM) is one of the most serious global diseases of cucurbit, apple, rose, grape and cereal crops. The ubiquitous disease creates considerable problems because it reduces the photosynthetic area of leaves, which in turn diminishes yield (50-100% in the absence of control) and product quality.

Worldwide costs associated with this disease are estimated by Dow AgroSciences to exceed US$100 million. Serious limitations with existing controls, namely DMI (demethylation-inhibiting) fungicide resistance, restrictions on the use of sulphur and sodium bicarbonate in organic systems, the lack of eradicant activity, and the lack efficacious organic alternatives, drive the need to find new control alternatives.

Brazilian (1) and Australian (2) researchers have reported that milk is as effective as conventional fungicides in the control of PM in squash and grape crops respectively. While the Brazilian research was conducted using fresh whole-milk, the Australians have reported that full-fat and skim milk powders, and whey and whey protein powders are effective. Neither group of researchers have reported the compound(s) responsible for the fungicidal activity or the mode of action. A wide range of milk components including salts, proteins, fats, calcium, and free radicals, are postulated to contribute to antifungal activity and/or stimulate biological control.

Fatty acids are reported to be toxic to diverse fungi and bacteria (3-5). The anti-fungal activity of plant oils (olive oil, canola oil, corn oil, grape seed oil, peanut oil, safflower oil, soya bean oil and sunflower oil) and mineral oils (JMS stylet oil) against powdery mildew has been reported (6-8).

Problems associated with using whole- or skim-milk products as fungicides include milk spoilage, development of unpleasant odours, handling difficulties, application problems, poor durability of control, and unwanted growth of other non-target organisms, e.g. sooty mould. Fungicides containing free fatty acids and/or plant or animal oils/fats can be expensive, clog agricultural spray equipment, provide only variable disease control, have phyto-toxic effects and may be restricted products in organic systems.

It is therefore an object of the invention to provide a fungicide that overcomes or ameliorates one or more of the problems with prior art fungicides, or that at least provides the public with a useful choice.

SUMMARY OF THE INVENTION

In a first aspect the invention provides a fungicidal composition comprising
(a) anhydrous milk fat (AMF) and optionally one or more of soybean oil, olive oil and coconut fat, and
(b) one or more of an agriculturally acceptable carrier, an emulsifier and an antioxidant.

In one embodiment the composition comprises:
(a) anhydrous milk fat and optionally one or more of soybean oil, olive oil and coconut fat,
(b) an emulsifier, and
(c) one or more of an agriculturally acceptable carrier and an antioxidant.

In one embodiment the composition comprises:
(a) anhydrous milk fat and optionally one or more of soybean oil, olive oil and coconut fat,
(b) an emulsifier, and
(c) water and optionally an antioxidant.

In one embodiment the composition is an aqueous composition comprising:
(a) anhydrous milk fat and optionally one or more of soybean oil, olive oil and coconut fat,
(b) an emulsifier, and
(c) water and optionally an antioxidant.

In one embodiment the composition comprises:
(a) anhydrous milk fat and optionally one or more of soybean oil, olive oil and coconut fat,
(b) an emulsifier,
(c) an antioxidant, and
(d) water.

In one embodiment the composition is an aqueous composition comprising:
(a) anhydrous milk fat and optionally one or more of soybean oil, olive oil and coconut fat,
(b) an emulsifier,
(c) an antioxidant, and
(d) water.

In a second aspect the invention provides a fungicidal composition comprising:
(a) soybean oil and optionally one or more of anhydrous milk fat (AMF), olive oil and coconut fat; and
(b) one or more of an agriculturally acceptable carrier, an emulsifier and an antioxidant.

In one embodiment of a composition of the invention comprising soybean oil wherein the composition comprises Tween 80 the composition further comprises an emulsifier.

In one embodiment of a composition of the invention comprising soybean oil it is provided that the composition does not comprise only soybean oil and Tween 80.

In a third aspect the invention provides a fungicidal composition comprising:
(a) coconut fat and optionally one or more of anhydrous milk fat (AMF), olive oil and soybean oil; and
(b) one or more of an agriculturally acceptable carrier, an emulsifier and an antioxidant.

In one embodiment the agriculturally acceptable carrier comprises water.

In one embodiment a composition of the invention is an aqueous composition.

In one embodiment a composition of the invention is a liquid composition.

In one embodiment a composition of the invention is liquid or solid concentrate.

In one embodiment a composition of the invention comprises at least about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 g/L of AMF and useful ranges may be selected between any of the foregoing values, for example, from about 10 to about 20 g/L. In one embodiment the composition comprises from about 1 g/L to about 30 g/L of AMF. In one embodiment the composition comprises from about 5 g/L to about 20 g/L of AMF. In one embodiment the composition comprises from about 5 g/L to about 15 g/L of AMF. In one embodiment the composition comprises from about 7 g/L to about 14 g/L of AMF.

In one embodiment a composition of the invention comprises at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0% weight by volume (w/v) of AMF and useful ranges may be selected between any of the foregoing values, for example, from about 1.0 to about 2.0% w/v. In one embodiment the composition comprises from about 0.1 to about 3.0% w/v of AMF. In one embodiment the composition comprises from about 0.5 to about 2.0% w/v of AMF. In one embodiment the composition comprises from about 0.5 to about 1.5% w/v of AMF. In one embodiment the composition comprises from about 0.7 to about 1.4% w/v of AMF.

In one embodiment a composition of the invention comprises at least about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 g/L of coconut fat and useful ranges may be selected between any of the foregoing values, for example, from about 10 to about 20 g/L. In one embodiment the composition comprises from about 1 g/L to about 30 g/L of coconut fat. In one embodiment the composition comprises from about 5 g/L to about 25 g/L of coconut fat. In one embodiment the composition comprises from about 7 g/L to about 20 g/L of coconut fat.

In one embodiment a composition of the invention comprises at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0% weight by volume (w/v) of coconut fat and useful ranges may be selected between any of the foregoing values, for example, from about 1.0 to about 2.0% w/v. In one embodiment the composition comprises from about 0.1 to about 3.0% w/v of coconut fat. In one embodiment the composition comprises from about 0.5 to about 2.5% w/v of coconut fat. In one embodiment the composition comprises from about 0.7 to about 2.0% w/v of coconut fat.

In one embodiment a composition of the invention comprises at least about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 ml/L of olive oil and useful ranges may be selected between any of the foregoing values, for example, from about 10 to about 20 ml/L. In one embodiment the composition comprises from about 1 ml/L to about 30 ml/L of olive oil. In one embodiment the composition comprises from about 5 ml/L to about 25 ml/L of olive oil.

In one embodiment the composition comprises from about 7 ml/L to about 20 ml/L of olive oil.

In one embodiment a composition of the invention comprises at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0% by volume (v/v) of olive oil and useful ranges may be selected between any of the foregoing values, for example, from about 1.0 to about 2.0% v/v. In one embodiment the composition comprises from about 0.1 to about 3.0% v/v of olive oil. In one embodiment the composition comprises from about 0.5 to about 2.5% v/v of olive oil. In one embodiment the composition comprises from about 0.7 to about 2.0% v/v of olive oil.

In one embodiment a composition of the invention comprises at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 ml/L of soybean oil and useful ranges may be selected between any of the foregoing values, for example, from about 10 to about 20 ml/L. In one embodiment the composition comprises from about 1 ml/L to about 40 ml/L of soybean oil. In one embodiment the composition comprises from about 5 ml/L to about 30 ml/L of soybean oil. In one embodiment the composition comprises from about 7 ml/L to about 20 ml/L of soybean oil.

In one embodiment a composition of the invention comprises at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 or 4.0% by volume (v/v) of soybean oil and useful ranges may be selected between any of the foregoing values, for example, from about 1.0 to about 2.0% v/v. In one embodiment the composition comprises from about 0.1 to about 4.0% v/v of soybean oil. In one embodiment the composition comprises from about 0.5 to about 3.0% v/v of soybean oil. In one embodiment the composition comprises from about 0.7 to about 2.0% v/v of soybean oil.

In one embodiment the emulsifier is selected from the group comprising glycerin fatty acid esters (monoglycerides, MG); mono- and di-glycerides (MG & DG) (e.g. Grindsted HV 40, Poem J-2021); distilled monoglycerides; citric acid esters of MG (CMG) (e.g. Grindsted Citrem N12 Veg™); diacetyl tartaric acid esters of mono- and di-glycerides (DATEMs) (e.g. Panodan AL 10™); polyglycerol esters of fatty acids (PGE) (e.g. Grindsted PGE 20 Veg™); polyglycerol polyricinoleate (PGPR) (e.g. Grindsted PGPR 90™); sorbitan esters of fatty acids (e.g. Palsgaard 7463™); sucrose esters of fatty acids; calcium stearoyl lactylates (e.g. Grindsted CSL P 80™); sodium stearoyl lactylates; lecithin (including enzyme digested lecithin); and caseinates (such as sodium caseinates including Alanate 191™).

In another embodiment the emulsifier is selected from the group comprising gums, preferably xanthan gum, preferably a xanthan gum from corn; a polysorbate 80; a composition comprising polyethylene oxide and oleic acid, preferably comprising 90% polyethylene oxide and 10% oleic acid (e.g. Palsgaard 7463™); sodium caseinate, preferably 93% sodium caseinate (e.g. Alanate 191™); and food grade mono- and di-glycerides derived from vegetable and animal fats but without addition of acids like tartatic acid (Grindsted HV 40™).

In one embodiment the emulsifier is selected from the group comprising citric acid esters of MG (CMG); diacetyl tartaric acid esters of mono- and di-glycerides (DATEMs) (e.g. Panodan AL 10™); polyglycerol esters of fatty acids (PGE); polyglycerol polyricinoleate (PGPR); calcium stearoyl lactylates; and lecithin (including enzyme digested lecithin).

In one embodiment a composition of the invention comprises at least about 0.5, 1, 1.5, 2, 2.5, 3, 3.5, 4, 4.5, 5, 5.5, 6, 6.5, 7, 7.5, 8, 8.5, 9, 9.5 or 10 g/L of an emulsifier and useful ranges may be selected between any of the foregoing values, for example, from about 5 g/L to about 8 g/L. In one embodiment the composition comprises from about 1 to about 10 g/L of an emulsifier. In one embodiment the composition comprises from about 3 g/L to about 5 g/L of an emulsifier.

In one embodiment a composition of the invention comprises at least about 0.05, or 1.0% weight by volume (w/v) of an emulsifier and useful ranges may be selected between any of the foregoing values, for example, from about 0.5 to about 0.8% w/v. In one embodiment the composition comprises from about 0.1 to about 1.0% w/v of an emulsifier. In one embodiment the composition comprises from about 0.3 to about 0.5% w/v of an emulsifier.

In one embodiment the antioxidant comprises one or more antioxidant agents selected from the group comprising ascorbyl palmitate (e.g. Grindox AP Kosher™), tocopherol (e.g. Grindox TOCO70™), alpha-tocopherol, rosemary extract, propyl gallate, tertiary butylhydroquinone (TBHQ) (e.g.

Grindox 204™), butylated hydroxyanisole (BHA), butylated hydroxytoluene (BHT) and chelating agents.

In another embodiment the antioxidant is selected from the group comprising a composition comprising propyl gallate and food-grade citric acid monoglyceride esters, preferably 20% propyl gallate and 80% food-grade citric acid monoglyceride ester (Grindox 122™); a composition comprising BHA and vegetable oil, preferably 20% BHA and 80% vegetable oil (Grindox 105™); and a rosemary extract comprising about 5% phenolic diterpenes (i.e. carnosic acid and carnosol) from Rosemarinus officinalis and 95% of a mixture comprising propylene glycol, mono- and di-glycerides of fatty acids, and acetic acid esters of mono- and di-glycerides of fatty acids (Guardian Rosemary Extract™).

In one embodiment a composition of the invention comprises at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5 or 5.0 g/L of an antioxidant and useful ranges may be selected between any of the foregoing values, for example, from about 0.5 g/L to about 1.5 g/L. In one embodiment the composition comprises from about 0.1 to about 5 g/L of an antioxidant. In one embodiment the composition comprises about 1 g/L of an antioxidant.

In one embodiment a composition of the invention comprises at least about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.25, 0.30, 0.35, 0.40, 0.45 or 0.50% weight by volume (w/v) of an antioxidant and useful ranges may be selected between any of the foregoing values, for example, from about 0.05 to about 0.15% w/v. In one embodiment the composition comprises from about 0.01 to about 0.5% w/v of an antioxidant. In one embodiment the composition comprises about 0.1% w/v of an antioxidant.

In one embodiment a composition of the invention comprises from about 1 g/L to about 30 g/L of AMF, from about 1 g/L to about 10 g/L of an emulsifier, from about 0.1 g/L to about 5 g/L of an antioxidant and optionally one or more of soybean oil, olive oil and coconut fat. In one embodiment the composition is an aqueous composition. In one embodiment the composition further comprises water.

In one embodiment a composition of the invention comprises from about 5 g/L to about 15 g/L of AMF, from about 2 g/L to about 6 g/L of an emulsifier, from about 0.5 g/L to about 1.5 g/L of an antioxidant and optionally one or more of soybean oil, olive oil and coconut fat. In one embodiment the composition is an aqueous composition. In one embodiment the composition further comprises water.

In one embodiment a composition of the invention comprises about 7 g/L to about 14 g/L of AMF, about 4 to 5 g/L of an emulsifier, about 1 g/L of an antioxidant and optionally one or more of soybean oil, olive oil and coconut fat. In one embodiment the composition is an aqueous composition. In one embodiment the composition further comprises water.

In one embodiment a composition of the invention is shelf stable.

In one embodiment a composition of the invention is sprayable and optionally further comprises one or more spray adjuvants.

In one embodiment a composition of the invention is formulated as a dip, a spray or a concentrate.

In one embodiment a composition of the invention may further comprise at least one additional agricultural agent. In an alternative embodiment a composition of the invention may be formulated for delivery separately, simultaneously or sequentially with at least one additional agricultural agent.

In one embodiment a composition of the invention may further comprise at least one additional fungicide. In an alternative embodiment a composition of the invention may be formulated for delivery separately, simultaneously or sequentially with at least one additional fungicide.

Preferred additional fungicides include but are not limited to natural fungicides, organic fungicides, sulphur-based fungicides, copper/calcium fungicides and elicitors of plant host defenses.

In one embodiment a composition of the invention is mildly phyto-toxic and preferably is not phyto-toxic.

In one embodiment a composition of the invention is able to prevent fungal infection. In another embodiment, a composition of the invention is able to prevent and control fungal infection. Preferably a composition of the invention is able to prevent or prevent and control infection caused by one or more pathogens selected from powdery mildew (PM), sooty mould, Botrytis mould, grape sour bunch rot, and banana leaf spot pathogens.

In one embodiment a composition of the invention is able to prevent or prevent and control infection caused by one or more pathogens selected from PM pathogens including *Sphaerotheca* pathogens such as *Sphaerotheca fuliginea*, *Erysiphe* pathogens such as *Erysiphe cichoracearum*, *Uncinula* pathogens such as *Uncinula necator*, *Erysiphe* pathogens such as *Erysiphe graminis* f. sp. *tritici*, *Sphaerotheca* pathogens such as *Sphaerotheca pannosa* var. *rosae* and *Podosphaera* pathogens such as *Podosphaera leucotricha*; Botrytis pathogens including *Botrytis cinerea*; sooty mould pathogens; grape sour bunch rot pathogens; downy mildew pathogens including *Plasmopara* pathogens such as *Plasmopara viticola*; and banana leaf spot pathogens including *Mycosphaerella* pathogens such as *Mycosphaerella fijiensis* (Black Sigatoka or Black Leaf Streak), *Mycosphaerella musicola* (Yellow Sigatoka) and *Mycosphaerella musae* (Speckle).

In one embodiment a composition of the invention is able to inhibit germination of fungal spores, preferably spores of one or more of *Botrytis cinerea, Cladosporium cladosporiodes*, and *Monilinia fructicola*.

In a fourth aspect the invention provides use of a composition of the invention in the manufacture of an agent for the prevention or control of fungal infection.

In a fifth aspect the invention provides use of a composition of the invention in the manufacture of an agent for the prevention or control of infection caused by one or more pathogens selected from powdery mildew (PM), sooty mould, Botrytis mould, grape sour bunch rot, and banana leaf spot pathogens, preferably PM pathogens including *Sphaerotheca* pathogens such as *Sphaerotheca fuliginea*, *Erysiphe* pathogens such as *Erysiphe cichoracearum*, *Uncinula* pathogens such as *Uncinula necator*, *Erysiphe* pathogens such as *Erysiphe graminis* f. sp. *tritici*, *Sphaerotheca* pathogens such as *Sphaerotheca pannosa* var. *rosae* and *Podosphaera* pathogens such as *Podosphaera leucotricha*; Botrytis pathogens including *Botrytis cinerea*; sooty mould pathogens; grape sour bunch rot pathogens; downy mildew pathogens including *Plasmopara* pathogens such as *Plasmopara viticola*; and banana leaf spot pathogens including *Mycosphaerella* pathogens such as *Mycosphaerella fijiensis* (Black Sigatoka or Black Leaf Streak), *Mycosphaerella musicola* (Yellow Sigatoka) and *Mycosphaerella musae* (Speckle).

In a sixth aspect the invention provides use of a composition of the invention in the manufacture of an agent that inhibits germination of fungal spores, preferably spores of one or more of *Botrytis cinerea, Cladosporium cladosporiodes*, and *Monilinia fructicola*.

In a seventh aspect the invention provides a method of preventing or controlling a fungal infection comprising application of a composition of the invention to a subject in need thereof.

In an eighth aspect the invention provides a method of preventing or controlling an infection caused by one or more pathogens selected from powdery mildew (PM), sooty mould, Botrytis mould, grape sour bunch rot, and banana leaf spot pathogens, preferably PM pathogens including *Sphaerotheca* pathogens such as *Sphaerotheca fuliginea*, *Erysiphe* pathogens such as *Erysiphe cichoracearum*, *Uncinula* pathogens such as *Uncinula necator*, *Erysiphe* pathogens such as *Erysiphe graminis* f sp. *tritici*, *Sphaerotheca* pathogens such as *Sphaerotheca pannosa* var. *rosae* and *Podosphaera* pathogens such as *Podosphaera leucotricha*; Botrytis pathogens including *Botrytis cinerea*; sooty mould pathogens; grape sour bunch rot pathogens; downy mildew pathogens including *Plasmopara* pathogens such as *Plasmopara viticola*; and banana leaf spot pathogens including *Mycosphaerella* pathogens such as *Mycosphaerella fijiensis* (Black Sigatoka or Black Leaf Streak), *Mycosphaerella musicola* (Yellow Sigatoka) and *Mycosphaerella musae* (Speckle), comprising application of a composition of the invention to a subject in need thereof.

In an ninth aspect the invention provides a method of inhibiting germination of fungal spores, preferably spores of one or more of *Botrytis cinerea*, *Cladosporium cladosporiodes*, and *Monilinia fructicola*, comprising application of a composition of the invention to a subject in need thereof.

In one embodiment a composition of the invention may be applied separately, simultaneously or sequentially with at least one additional agricultural agent.

In one embodiment a composition of the invention may be applied separately, simultaneously or sequentially with at least one additional fungicide.

In one embodiment the subject comprises a plant, plant material or any surface that may contact harvested crops including harvesting equipment, packaging equipment and packaging material.

In one embodiment of a method of the invention the composition is applied at least about every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 60, 90, 120, 150 or 180 days. In one embodiment the composition is applied about every 1 to about every 7 days, about every 1 to about every 14 days, about every 1 to about every 21 days, about every 1 to about every 28 days or about every 1 to about every 35 days. In one embodiment the composition is applied about every 1 to about every 30 days, about every 1 to about every 60 days or about every 1 to about every 90 days. In one embodiment the composition is applied about every 1 to about every 7 days, about every 7 to about every 14 days, about every 14 to about every 21 days, about every 21 to about every 28 days or about every 28 to about every 35 days.

The term "comprising" means "consisting at least in part of"; that is to say when interpreting statements in this specification and claims which include that term, the features prefaced by that term in each statement all need to be present but other features can also be present.

The term "weight by volume" (w/v) refers to the mass (in grams) of a substance dissolved in or mixed with 100 milliliters of solution or mixture. Thus 1% w/v is equal to 1 gram per deciliter (g/dL) or 10 grams per liter (g/L).

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

DETAILED DESCRIPTION OF THE INVENTION

Figure 1:
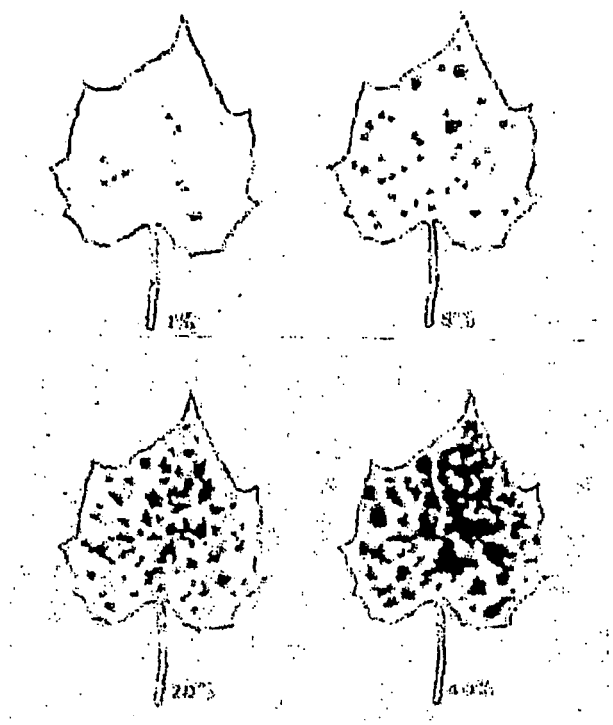
FIG. 1 shows the Powdery Mildew leaf standard area diagrams from Spencer (9).

As discussed above, the present invention relates in one aspect to a fungicidal composition comprising anhydrous milk fat (AMF) and optionally one or more of soybean oil, olive oil and coconut fat; and one or more of a carrier, an emulsifier and an antioxidant.

In another aspect the present invention relates to a fungicidal composition comprising soybean oil and optionally one or more of AMF, olive oil and coconut fat; and one or more of a carrier, an emulsifier and an antioxidant. Preferably the one or more of a carrier, an emulsifier and an antioxidant is not only Tween 80.

In another aspect the present invention relates to a fungicidal composition comprising coconut fat and optionally one or more of soybean oil, olive oil and AMF; and one or more of a carrier, an emulsifier and an antioxidant.

The term "anhydrous milk fat" (AMF) as used herein is intended to mean a substantially anhydrous composition comprising at least about 85, 85.5, 86, 86.5, 87, 87.5, 88, 88.5, 89, 89.5, 90, 90.5, 91, 91.5, 92, 92.5, 93, 93.5, 94, 94.5, 95, 95.5, 96, 96.5, 97, 97.5, 98, 98.5 or 99% milk fat by weight, preferably 99.1, 99.2, 99.3, 99.4, 99.5, 99.6, 99.7, 99.8 or 99.9% milk fat by weight, and useful ranges may be selected between any of the foregoing values, for example, from about 85.5 to about 99.8% milk fat by weight.

In one embodiment AMF is produced by separation and phase-inversion of cream.

In one embodiment AMF is produced by concentrating cream to 70 to 80% milk fat by subjecting cream to centrifugal separation. The resulting oil-in-water emulsion is then subjected to phase inversion. Phase inversion is carried out to produce a water-in-oil emulsion using a device able to mechanically shear fat membranes.

In one embodiment the water-in-oil emulsion is subjected to a centrifugation step to produce a composition comprising 95 to 99% milk fat.

In one embodiment the 95 to 99% milk fat composition is subjected to a centrifugation step to produce a composition comprising 99 to 99.5% milk fat.

In one embodiment the 99 to 99.5% milk fat composition is dehydrated under vacuum to produce an AMF composition comprising about 99.8% fat.

Accordingly, reference to "anhydrous milk fat" (AMF) herein is intended to include milk fat compositions produced during the course of AMF production ("AMF precursors").

The compositions of the invention, in various embodiments, are sprayable and may be sprayed onto a subject in need thereof, or formulated as a concentrate that is sprayable on addition of agriculturally acceptable carriers and/or spray adjuvants. Preferred compositions of the invention are shelf stable. The term "shelf stable" is intended to mean that a composition of the invention does not separate out into separate phases or develop any offensive odours.

The term "agriculturally acceptable carrier" intended to include any material that facilitates application of a composition of the invention to the intended subject, which may for example be a plant, plant material or equipment, or that facilitates storage, transport or handling. Carriers used in compositions for application to plants and plant material are preferably non-phytotoxic or only mildly phytotoxic. A suitable carrier may be a solid, liquid or gas depending on the desired formulation. In one embodiment preferred carriers include polar liquid carriers such as water, mineral oils and vegetable oils.

Examples of liquid carriers include but are not limited to water; alcohols, particularly butanol or glycol, as well as their ethers or esters, particularly methylglycol acetate; ketones, particularly acetone, cyclohexanone, methylethyl ketone, methylisobutylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar solvents such as dimethylformamide, dimethyl sulfoxide, or N-methylpyrrolidone; liquefied gases; or the like or a mixture thereof.

Examples of solid carriers include but are not limited to fillers such as kaolin, bentonite, dolomite, calcium carbonate, talc, powdered magnesia, Fuller's earth, gypsum, diatomaceous earth and China clay.

A carrier which provides for slow or delayed release of a compound of the invention may also be included in a composition of the invention.

The compositions of the invention, in various embodiments, preferably mitigate, ameliorate or avoid at least one problem associated with existing fungicides such as spoilage of whole or skim milk based products, development of unpleasant odours, handling difficulties, application problems, poor durability of control, unwanted growth of other non-target organisms such as sooty mould, expense, variability of disease control, phytotoxicity and regulatory restrictions.

In one embodiment, a composition of the invention is able to prevent fungal infection. In another embodiment, a composition of the invention is able to prevent and control fungal infection. Preferably a composition of the invention is able to prevent or prevent and control infection caused by one or more pathogens selected from powdery mildew (PM), sooty mould, Botrytis mould, grape sour bunch rot, and banana leaf spot pathogens.

As used herein, the term "control fungal infection" is intended to mean at least maintaining, preferably maintaining or reducing, and more preferably reducing, the degree of infection by a pathogen including but not limited to the pathogens listed below. In one embodiment, "control fungal infection" preferably means the composition is able to substantially eradicate an existing fungal infection by a pathogen including but not limited to the pathogens listed below.

In one embodiment, a composition of the invention is able to prevent or prevent and control infection caused by one or more pathogens including but not limited to PM pathogens including *Sphaerotheca* pathogens such as *Sphaerotheca fuliginea*, *Erysiphe* pathogens such as *Erysiphe cichoracearum* (cucurbit PM), *Uncinula* pathogens such as *Uncinula necator* (grape PM), *Erysiphe* pathogens such as *Erysiphe graminis* f sp. *Tritici* (wheat PM), *Sphaerotheca* pathogens such as *Sphaerotheca* pannosa var. *rosae* (rose PM) and *Podosphaera* pathogens such as *Podosphaera leucotricha* (apple PM); Botrytis pathogens including *Botrytis cinerea* (grey mould on grape); sooty mould pathogens (including *Cladosporium cladosporiodes*); grape sour bunch rot pathogens (a complex of fungi e.g. *Penicillium* spp., *Aspergillus* spp., yeasts (e.g. *Candida krusei*), and acetic acid bacteria (e.g. *Acetobacter* spp.) that cause a wet rot on grape bunches); downy mildew pathogens including *Plasmopara* pathogens such as *Plasmopara viticola*; and banana leaf spot pathogens including *Mycosphaerella* pathogens such as *Mycosphaerella fijiensis* (Black Sigatoka or Black Leaf Streak), *Mycosphaerella musicola* (Yellow Sigatoka) and *Mycosphaerella musae* (Speckle).

In another embodiment, a composition of the invention is able to inhibit germination of fungal spores, preferably spores of one or more of *Botrytis cinerea, Cladosporium cladosporiodes*, and *Monilinia fructicola*.

Thus, the present invention also relates to use of a composition of the invention in manufacture of an agent for the prevention or control of fungal infection, preferably a fungal infection caused by one or more of the pathogens listed above, and use in the manufacture of an agent that inhibits the germination of one or more of the pathogens list above.

The invention also relates to a method of preventing or controlling a fungal infection, preferably a fungal infection caused by one or more of the pathogens listed above, comprising application of a composition of the invention to a subject in need thereof.

The invention also relates to a method of inhibiting germination of fungal spores, preferably fungal spores of one or more of the pathogens listed above, comprising application of a composition of the invention to a subject in need thereof.

As used herein, the term "subject" is intended to include any target surface to which a compound or composition of the invention may be applied, for example to a plant, plant material including roots, bulbs, tubers, corms, leaves, flowers, seeds, stems, callus tissue, nuts, grains, fruit, cuttings, root stock, scions, harvested crops including roots, bulbs, tubers, corms, leaves, flowers, seeds, stems, callus tissue, nuts, grains, fruit, cuttings, root stock, scions, or any surface that may contact harvested crops including harvesting equipment, packaging equipment and packaging material.

In one embodiment, the subject comprises a plant, plant material or any surface that may contact harvested crops including harvesting equipment, packaging equipment and packaging material. For surfaces such as harvesting equipment, packaging equipment and packaging material, preferably a composition of the invention is applied immediately before use of the harvesting equipment, packaging equipment or packaging material.

In one embodiment, a composition of the invention is formulated as a dip, a spray or a concentrate.

In one embodiment, a composition of the invention may further comprise at least one additional agricultural agent. In an alternative embodiment a composition of the invention may be delivered separately, simultaneously or sequentially with at least one additional agricultural agent.

In one embodiment, a composition of the invention may further comprise at least one additional fungicide. In an alternative embodiment a composition of the invention may be delivered separately, simultaneously or sequentially with at least one additional fungicide.

When formulating a composition of the invention containing an additional agricultural agent such as an additional fungicide or planning delivery of a composition of the invention separately, simultaneously or sequentially with an additional agricultural agent such as an additional fungicide it may be desirable to assess the degree of phytotoxicity resulting from application of the compositions to plant material over time. This may be assessed according to the methodology presented in the examples below.

Assessment of a composition of the invention or a composition of the invention including or delivered with an additional agricultural agent such as an additional fungicide may include assessment of:
(1) Degree of control of target microbes without stimulating growth of undesirable non-target microbes or harming beneficial organisms.
(2) Durability of control.
(3) Degree of phytotoxicity and effects on plant development when used repeatedly throughout a portion or the entirety of a growing season.
(4) Compatibility with other control products used in the industry.

In one embodiment, the composition comprises at least about 1 g/L, preferably from about 1 g/L to about 30 g/L, and more preferably about 5 g/L to about 20 g/L of AMF. In a highly preferred embodiment, the composition comprises about 7 g/L to about 14 g/L of AMF.

In one embodiment, the composition comprises at least about 1 g/L, preferably from about 1 g/L to about 30 g/L, and more preferably about 5 g/L to about 25 g/L of coconut fat. In a highly preferred embodiment, the composition comprises about 7 g/L to about 20 g/L of coconut fat.

In one embodiment, the composition comprises at least about 1 ml/L, preferably from about 1 ml/L to about 30 ml/L, and more preferably about 5 ml/L to about 25 ml/L of olive oil. In a highly preferred embodiment, the composition comprises about 7 ml/L to about 20 ml/L of olive oil.

In one embodiment, the composition comprises at least about 1 ml/L, preferably from about 1 ml/L to about 40 ml/L, and more preferably about 5 ml/L to about 30 ml/L of soybean oil. In a highly preferred embodiment, the composition comprises about 7 ml/L to about 20 ml/L of soybean oil.

Emulsifiers useful herein include but are not limited to glycerin fatty acid esters (monoglycerides, MG); mono- and di-glycerides (MG & DG) (e.g. Grindsted HV 40™, Poem J-2021™); distilled monoglycerides; citric acid esters of MG (CMG); diacetyl tartaric acid esters of mono- and di-glycerides (DATEMs) (e.g. Panodan AL 10™); polyglycerol esters of fatty acids (PGE); polyglycerol polyricinoleate (PGPR); sorbitan esters of fatty acids (e.g. Palsgaard 7463™); sucrose esters of fatty acids; calcium stearoyl lactylates; sodium stearoyl lactylates; lecithin (including enzyme digested lecithin); and caseinates (such as sodium caseinates including Alanate 191™).

Preferred emulsifiers include diacetyl tartaric acid esters of mono- and di-glycerides (DATEMs) which are GRAS (generally regarded as safe by the FDA or EEC) emulsifiers for foodstuffs. DATEMs are formed by reacting diacetyltartaric anhydride with partial glycerides of edible oils, fats or fat-forming fatty acids. Sources of glycerides for the production of DATEMs include soy oil, palm oil, sunflower oil, beef tallow and monoglycerides. DATEMs may be obtained commercially from, for example, Danisco Ingredients.

DATEMs are made using standard techniques well known in the art (see for example, Schuster and Adams, Rev. Fr. Corps Gras, 29(9):357-365, 1981) and those produced from glycerides of edible fats or from fatty acids may exist in a variety of isomeric forms (see for example, Food Emulsions, Second Edition, Revised and Expanded, ed. By Larsson and Friberg, Marcel Dekker, Inc., New York, 1990).

A highly preferred DATEM, Panodan AL 10™ comprises diacetyl tartaric acid esters of mono- and di-glycerides derived from food grade vegetable and/or animal triglycerides, preferably soybean oil triglycerides and may include glycerides comprising lauric, palmitic, stearic, oleic, linoleic and/or linolenic acids.

In another embodiment, the emulsifier is selected from the group comprising gums, preferably xanthan gum, preferably a xanthan gum from corn; a polysorbate 80; a composition comprising polyethylene oxide and oleic acid, preferably comprising 90% polyethylene oxide and 10% oleic acid (Palsgaard 7463™); sodium caseinate, preferably 93% sodium caseinate (Alanate 191™); and food grade mono- and di-glycerides derived from vegetable and animal fats (but without addition of acids like tartatic acid) (Grindsted HV 40™).

In one embodiment, the composition comprises at least about 0.5 g/L, preferably about 1 to about 10 g/L and more preferably about 3 g/L to about 5 g/L of emulsifier.

In one embodiment, the antioxidant comprises one or more antioxidant agents selected from ascorbyl palmitate (e.g. Grindox AP Kosher™), tocopherol (e.g. Grindox T00070™), alpha-tocopherol, rosemary extract, propyl gallate, tertiary butylhydroquinone (TBHQ) (e.g. Grindox 204™), butylated hydroxyanisole (BHA), butylated hydroxytoluene (BHT) and chelating agents.

In another embodiment, the antioxidant is selected from the group comprising a composition comprising propyl gallate and food-grade citric acid monoglyceride esters, preferably 20% propyl gallate and 80% food-grade citric acid monoglyceride ester (Grindox 122™); a composition comprising BHA and vegetable oil, preferably 20% BHA and 80% vegetable oil (Grindox 105™); and a rosemary extract comprising about 5% phenolic diterpenes (i.e. carnosic acid and carnosol) from Rosemarinus officinalis and 95% of a mixture comprising propylene glycol, mono- and di-glycerides of fatty acids, and acetic acid esters of mono- and di-glycerides of fatty acids (Guardian Rosemary Extract™).

In one embodiment, the compositions comprises at least about 0.1 g/L, preferably about 0.1 to about 5 g/L and more preferably about 1 g/L of antioxidant.

In one embodiment, preferably the composition comprises about 5 to 20 g/L of AMF, about 5 g/L of emulsifier, about 1 g/L of antioxidant and optionally one or more of soybean oil, olive oil and coconut fat.

In one embodiment a composition of the invention is an aqueous composition.

In one embodiment a composition of the invention is a liquid composition.

Formulation of a liquid composition of the invention comprising AMF or coconut fat preferably comprises melting the fat, preferably by heating to about 40° C., combining an emulsifier with the molten fat then mixing the emulsified molten fat with water, preferably water that is at about 40 to 90° C., under shear conditions to produce an oil-in-water emulsion.

Formulation of a liquid composition of the invention comprising soybean oil preferably comprises warming the oil, preferably to about 40° C., combining an emulsifier with the warmed oil then mixing the emulsified oil with water, preferably water that is at about 40 to 90° C., under shear conditions to produce an oil-in-water emulsion.

In one embodiment a composition of the invention is a solid composition.

Formulation of a solid composition of the invention preferably comprises spray-drying or freeze-drying a composition of the invention or adsorbing a composition of the invention into an adsorbent.

In one embodiment a composition of the invention is a concentrate, preferably a liquid concentrate (including but not limited to an aqueous concentrate) or solid concentrate.

The invention also provides a water soluble sachet comprising a composition of the invention, preferably a concentrate of the invention.

In one embodiment a composition of the invention comprises at least about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 g/L of AMF and useful ranges may be selected between any of the foregoing values, for example, from about 10 to about 20 g/L. In one embodiment the composition comprises from about 1 g/L to about 30 g/L of AMF. In one embodiment the composition comprises from about 5 g/L to about 20 g/L of AMF. In one embodiment the composition comprises from about 5 g/L to about 15 g/L of AMF. In one embodiment the composition comprises from about 7 g/L to about 14 g/L of AMF.

In one embodiment a composition of the invention comprises at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0% weight by volume (w/v) of AMF and useful ranges may be selected between any of the foregoing values, for example, from about 1.0 to about 2.0% w/v. In one embodiment the composition comprises from about 0.1 to about 3.0% w/v of AMF. In one embodiment the composition comprises from about 0.5 to about 2.0% w/v of AMF. In one embodiment the composition comprises from about 0.5 to about 1.5% w/v of AMF. In one embodiment the composition comprises from about 0.7 to about 1.4% w/v of AMF.

In one embodiment a composition of the invention comprises at least about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 g/L of coconut fat and useful ranges may be selected between any of the foregoing values, for example, from about 10 to about 20 g/L. In one embodiment the composition comprises from about 1 g/L to about 30 g/L of coconut fat. In one embodiment the composition comprises from about 5 g/L to about 25 g/L of coconut fat. In one embodiment the composition comprises from about 7 g/L to about 20 g/L of coconut fat.

In one embodiment a composition of the invention comprises at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0% weight by volume (w/v) of coconut fat and useful ranges may be selected between any of the foregoing values, for example, from about 1.0 to about 2.0% w/v. In one embodiment the composition comprises from about 0.1 to about 3.0% w/v of coconut fat. In one embodiment the composition comprises from about 0.5 to about 2.5% w/v of coconut fat. In one embodiment the composition comprises from about 0.7 to about 2.0% w/v of coconut fat.

In one embodiment a composition of the invention comprises at least about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 ml/L of olive oil and useful ranges may be selected between any of the foregoing values, for example, from about 10 to about 20 ml/L. In one embodiment the composition comprises from about 1 ml/L to about 30 ml/L of olive oil. In one embodiment the composition comprises from about 5 ml/L to about 25 ml/L of olive oil. In one embodiment the composition comprises from about 7 ml/L to about 20 ml/L of olive oil.

In one embodiment a composition of the invention comprises at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0% by volume (v/v) of olive oil and useful ranges may be selected between any of the foregoing values, for example, from about 1.0 to about 2.0% v/v. In one embodiment the composition comprises from about 0.1 to about 3.0% v/v of olive oil. In one embodiment the composition comprises from about 0.5 to about 2.5% v/v of olive oil. In one embodiment the composition comprises from about 0.7 to about 2.0% v/v of olive oil.

In one embodiment a composition of the invention comprises at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 ml/L of soybean oil and useful ranges may be selected between any of the foregoing values, for example, from about 10 to about 20 ml/L. In one embodiment the composition comprises from about 1 ml/L to about 40 ml/L of soybean oil. In one embodiment the composition comprises from about 5 ml/L to about 30 ml/L of soybean oil. In one embodiment the composition comprises from about 7 ml/L to about 20 ml/L of soybean oil.

In one embodiment a composition of the invention comprises at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 or 4.0% by volume (v/v) of soybean oil and useful ranges may be selected between any of the foregoing values, for example, from about 1.0 to about 2.0% v/v. In one embodiment the composition comprises from about 0.1 to about 4.0% v/v of soybean oil. In one embodiment the composition comprises from about 0.5 to about 3.0% v/v of soybean oil. In one embodiment the composition comprises from about 0.7 to about 2.0% v/v of soybean oil.

In one embodiment a composition of the invention comprises at least about 0.5, 1, 1.5, 2, 2.5, 3, 3.5, 4, 4.5, 5, 5.5, 6, 6.5, 7, 7.5, 8, 8.5, 9, 9.5 or 10 g/L of an emulsifier and useful ranges may be selected between any of the foregoing values, for example, from about 5 g/L to about 8 g/L. In one embodiment the composition comprises from about 1 to about 10 g/L of an emulsifier. In one embodiment the composition comprises from about 3 g/L to about 5 g/L of an emulsifier.

In one embodiment a composition of the invention comprises at least about 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95 or 1.0% weight by volume (w/v) of an emulsifier and useful ranges may be selected between any of the foregoing values, for example, from about 0.5 to about 0.8% w/v.

In one embodiment the composition comprises from about 0.1 to about 1.0% w/v of an emulsifier. In one embodiment the composition comprises from about 0.3 to about 0.5% w/v of an emulsifier.

In one embodiment a composition of the invention comprises at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5 or 5.0 g/L of an antioxidant and useful ranges may be selected between any of the foregoing values, for example, from about 0.5 g/L to about 1.5 g/L. In one embodiment the composition comprises from about 0.1 to about 5 g/L of an antioxidant.

In one embodiment the composition comprises about 1 g/L of an antioxidant.

In one embodiment a composition of the invention comprises at least about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.25, 0.30, 0.35, 0.40, 0.45 or 0.50% weight by volume (w/v) of an antioxidant and useful ranges may be selected between any of the foregoing values, for example, from about 0.05 to about 0.15% w/v. In one embodiment the composition comprises from about 0.01 to about 0.5% w/v of an antioxidant. In one embodiment the composition comprises about 0.1% w/v of an antioxidant.

In one embodiment a composition of the invention comprises at least about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 g/L of at least one additional agricultural agent, preferably an additional fungicide and useful ranges may be selected between any of the foregoing values, for example, from about 10 to about 20 g/L.

In one embodiment a composition of the invention comprises at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0% weight by volume (w/v) of at least one additional agricultural agent, preferably an additional fungicide and useful ranges may be selected between any of the foregoing values, for example, from about 1.0 to about 2.0% w/v.

A concentrate of the invention may include an agriculturally acceptable carrier, may require addition of an agriculturally acceptable carrier or may require addition of a further amount of an agriculturally acceptable carrier that is already present in the concentrate in a lesser amount.

In one embodiment a concentrate of the invention is formulated so that when the concentrate is diluted for use the resulting composition provides an AMF, coconut fat, olive oil, soybean oil, emulsifier and/or antioxidant concentration selected from the concentrations listed above.

In one embodiment a concentrate of the invention comprises at least about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 g of AMF.

In one embodiment a concentrate of the invention comprises at least about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 g of coconut fat.

In one embodiment a concentrate of the invention comprises at least about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 ml of olive oil.

In one embodiment a concentrate of the invention comprises at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 ml of soybean oil.

In one embodiment a concentrate of the invention comprises at least about 0.5, 1, 1.5, 2, 2.5, 3, 3.5, 4, 4.5, 5, 5.5, 6, 6.5, 7, 7.5, 8, 8.5, 9, 9.5 or 10 g of an emulsifier.

In one embodiment a concentrate of the invention comprises at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5 or 5.0 g of an antioxidant.

In one embodiment a concentrate of the invention comprises at least about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 g of at least one additional agricultural agent, preferably an additional fungicide.

In one embodiment, a composition of the invention is mildly phyto-toxic and preferably the composition is not phyto-toxic.

As used herein, the term "mildly phyto-toxic" is intended to mean that the level of phyto-toxicity does not substantially effect plant yield or quality and preferably means that a composition of the invention may cause small blemishes (5-15 $mm^2$) on plant leaves, and may cause necrotic or chlorotic patches (>15 $mm^2$) and leaf distortion, but preferably should not kill more than 30%, preferably not more than 20% of a leaf on a plant to which a composition of the invention is applied. The term "plant yield" is intended to refer to the product yield of a plant or population of plants. In one embodiment the yield may be the yield of a product including but not limited to one or more of whole plants or plant parts such as roots, bulbs, corms, tubers, leaves, cuttings, flowers, stems, fruits and seeds or other propagative material.

In one embodiment of a method of the invention the composition is applied at least about every 1, 2, 3, 4, 5, 6, 7, 8, 9, 10, 11, 12, 13, 14, 15, 16, 17, 18, 19, 20, 21, 22, 23, 24, 25, 26, 27, 28, 29; 30, 60, 90, 120, 150 or 180 days. In one embodiment the composition is applied about every 1 to about every 7 days, about every 1 to about every 14 days, about every 1 to about every 21 days, about every 1 to about every 28 days or about every 1 to about every 35 days. In one embodiment the composition is applied about every 1 to about every 30 days, about every 1 to about every 60 days or about every 1 to about every 90 days. In one embodiment the composition is applied about every 1 to about every 7 days, about every 7 to about every 14 days, about every 14 to about every 21 days, about every 21 to about every 28 days or about every 28 to about every 35 days.

In one embodiment of a method of the invention the composition is applied at least about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 times per season.

In one embodiment the subject is grape vines and a composition of the invention may be applied up to within 6 weeks of harvest (pre-vintage).

In one embodiment the subject is a squash plant and a composition of the invention may be applied within the first half of the season.

In one embodiment the subject is an apple seedling and a composition of the invention may be applied throughout the seedling stage.

In one embodiment of a method of the invention a composition of the invention is delivered separately, simultaneously or sequentially with at least one additional agricultural agent.

In one embodiment a method of the invention comprises application of a composition of the invention to a surface in need thereof for a first period and application of at least one additional agricultural agent to the surface for a second period. In another embodiment a method of the invention comprises application of at least one additional agricultural agent to a surface in need thereof for a first period and application of a composition of the invention to the surface for a second period.

In one embodiment of a method of the invention a composition of the invention is delivered separately, simultaneously or sequentially with at least one additional fungicide.

In one embodiment a method of the invention comprises application of a composition of the invention to a surface in need thereof for a first period and application of at least one additional fungicide to the surface for a second period. In another embodiment a method of the invention comprises application of at least one additional fungicide to a surface in need thereof for a first period and application of a composition of the invention to the surface for a second period. In one embodiment the method of this embodiment results in a degree of control of the target pathogen substantially similar to or greater than that obtainable through use of the additional fungicide alone, while avoiding the need to use the additional fungicide throughout the entire growing season.

In one embodiment the subject comprises grape vines and the first period comprises the first half of a growing season or a period selected from the periods up to pre-capfall, 5% capfall, 90% capfall, post bloom, berries pea size, pre-bunch closure, post bunch closure or veraison. In a preferred embodiment the first period comprises the growing season up to veraison.

In one embodiment the subject comprises grape vines and the second period comprises the second half of a growing season or a period selected from the periods following veraison, 4 weeks pre-vintage or 2 weeks pre-vintage.

The compositions of the invention can be applied to a subject in a number of ways, for example, they can be applied directly to plant parts such as roots, bulbs, corms, tubers, leaves, cuttings, flowers, stems, fruits and/or the foliage of a tree, or to seeds or other propagative material, or to other medium in which the trees are growing or are to be planted, or they can be sprayed on or dusted on.

In one embodiment an agriculturally acceptable carrier can be solid or liquid. Carriers useful herein include any substance typically used to formulate agricultural composition.

In one embodiment the agriculturally acceptable carrier maybe selected from the group comprising fillers, solvents, excipients, surfactants, suspending agents, speaders/stickers (adhesives), antifoaming agents, dispersants, wetting agents, drift reducing agents, auxiliaries, adjuvants or a mixture thereof.

Compositions of the invention may be formulated as, for example, concentrates, solutions, sprays, aerosols, immersion baths, dips, emulsions, wettable powders, soluble powders, suspension concentrates, dusts, granules, water dispersible granules, microcapsules, pastes, gels and other formulation types by well-established procedures.

These procedures include mixing and/or milling of the active ingredients with agriculturally acceptable carrier substances, such as fillers, solvents, excipients, surfactants, suspending agents, speaders/stickers (adhesives), antifoaming agents, dispersants, wetting agents, drift reducing agents, auxiliaries and adjuvants.

In one embodiment solid carriers include but are not limited to mineral earths such as silicic acids, silica gels, silicates, talc, kaolin, attapulgus clay, limestone, lime, chalk, bole, loess, clay, dolomite, diatomaceous earth, aluminas calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders and the like. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black; water soluble polymers, resins, waxes; or solid fertilizers. Such solid compositions may, if desired, contain one or more compatible wetting, dispersing, emulsifying or coloring agents which, when solid, may also serve as a diluent.

In one embodiment the carrier may also be liquid, for example, water; alcohols, particularly butanol or glycol, as well as their ethers or esters, particularly methylglycol acetate; ketones, particularly acetone, cyclohexanone, methylethyl ketone, methylisobutylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar solvents such as dimethylformamide, dimethyl sulfoxide, or N-methylpyrrolidone; liquefied gases; or the like or a mixture thereof.

In one embodiment surfactants include nonionic surfactants, anionic surfactants, cationic surfactants and/or amphoteric surfactants and promote the ability of aggregates to remain in solution during spraying.

Spreaders/stickers promote the ability of the compositions of the invention to adhere to plant surfaces. Examples of surfactants, spreaders/stickers include but are not limited to Tween and Triton (Rhom and Hass Company), Fortune®, Pulse, C. Daxoil, Codacide Oil®, D-C talc, Supamet Oil, Bond®, Penetrant, Glowelt® and Freeway, alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Wetting agents reduce surface tension of water in the composition and thus increase the surface area over which a given amount of the composition may be applied. Examples of wetting agents include but are not limited to salts of polyacrylic acids, salts of lignosulfonic acids, salts of phenolsulfonic or naphthalenesulfonic acids, polycondensates of ethylene oxide with fatty alcohols or fatty acids or fatty esters or fatty amines, substituted phenols (particularly alkylphenols or arylphenols), salts of sulfosuccinic acid esters, taurine derivatives (particularly alkyltaurates), phosphoric esters of alcohols or of polycondensates of ethylene oxide with phenols, esters of fatty acids with polyols, or sulfate, sulfonate or phosphate functional derivatives of the above compounds.

In one embodiment the preferred method of applying the compound or composition of the invention is to spray a dilute or concentrated solution by handgun or commercial airblast.

As described above, the compositions of the present invention may be used alone or in combination with one or more other agricultural agents, including pesticides, insecticides, acaracides, additional fungicides, bactericides, herbicides, antibiotics, antimicrobials, nemacides, rodenticides, entomopathogens, phermones, attractants, plant growth regulators, plant hormones, insect growth regulators, chemosterilants, microbial pest control agents, repellents, viruses, phagostimulents, plant nutrients, plant fertilisers and biological controls. When used in combination with other agricultural agents the administration of the two agents may be separate, simultaneous or sequential. Specific examples of these agricultural agents are known to those skilled in the art, and many are readily commercially available.

Examples of plant nutrients include but are not limited to nitrogen, magnesium, calcium, boron, potassium, copper, iron, phosphorus, manganese, molybdenum, cobalt, boron, copper, silicon, selenium, nickel, aluminum, chromium and zinc.

Examples of antibiotics include but are not limited to oxytetracyline and streptomycin.

Examples of fungicides include but are not limited to the following classes of fungicides: carboxamides, benzimidazoles, triazoles, hydroxypyridines, dicarboxamides, phenylamides, thiadiazoles, carbamates, cyano-oximes, cinnamic acid derivatives, morpholines, imidazoles, beta-methoxy acrylates and pyridines/pyrimidines.

Further examples of fungicides include but are not limited to natural fungicides, organic fungicides, sulphur-based fungicides, copper/calcium fungicides and elicitors of plant host defences.

Examples of natural fungicides include but are not limited to whole milk, whey, fatty acids or esterified fatty acids.

Examples of organic fungicides include but are not limited to any fungicide which passes an organic certification standard such as biocontrol agents, natural products, elicitors (some of may also be classed as natural products), and sulphur and copper fungicides (limited to restricted use).

An example of a sulphur-based fungicide is Kumulus™ DF (BASF, Germany).

An example of a copper fungicide is Kocide® 2000 DF (Griffin Corporation, USA).

Examples of elicitors include but are not limited to chitosan, Bion™, BABA (DL-3-amino-n-butanoic acid, β-aminobutyric acid) and Milsana™ (Western Farm Service, Inc., USA).

In some embodiments non-organic fungicides may be employed. Examples of non-organic fungicides include but are not limited to Bravo™ (for control of PM on cucurbits); Supershield™ (Yates, NZ) (for control of Botrytis and PM on roses); Topas® 200EW (for control of PM on grapes and cucurbits); Flint™ (for control of PM on apples and cucurbits); Amistar® WG (for control of rust and PM on cereals); and Captan™, Dithane™, Euparen™, Rovral™, Scala™, Shirlan™, Switch™ and Teldor™ (for control of Botrytis on grapes).

Examples of pesticides include but are not limited to azoxystrobin, bitertanol, carboxin, $Cu_2O$, cymoxanil, cyproconazole, cyprodinil, dichlofluamid, difenoconazole, diniconazole, epoxiconazole, fenpiclonil, fludioxonil, fluquiconazole, flusilazole, flutriafol, furalaxyl, guazatin, hexaconazole, hymexazol, imazalil, imibenconazole, ipconazole, kresoxim-methyl, mancozeb, metalaxyl, R-metalaxyl, metconazole, oxadixyl, pefurazoate, penconazole, pencycuron, prochloraz, propiconazole, pyroquilone, SSF-109, spiroxamin, tebuconazole, thiabendazole, tolifluamid, triazoxide, triadimefon, triadimenol, triflumizole, triticonazole and uniconazole.

An example of a biological control is the BotryZen™ biological control agent comprising *Ulocladium oudemansii*.

The efficacy of compositions of the invention may be confirmed using an assay system such as that described in the Examples.

Efficacy of compositions of the invention may also be confirmed using field trial assay systems. For example, confirmation of the ability of compositions of the invention to prevent fungal growth may be obtained by applying a compound or composition of the invention to plant material and then inoculating with a target organism. Efficacy is confirmed by the absence of growth or less growth of the target organism than an untreated control.

Confirmation of the ability of compositions of the invention to treat fungal growth may be obtained by inoculating plant material with a target organism and then applying a composition of the invention. Efficacy is confirmed by a reduction in the degree of growth or the disappearance of the target organism compared to an untreated control.

Various aspects of the invention will now be illustrated in non-limiting ways by reference to the following examples.

EXAMPLES

Trial 1—Materials and Methods

Squash (*Cucurbita maxima*) cv 'Delica' and Zucchini (*Cucurbita pepo*) cv 'Black Jack' were potted in 80% bark 20% pumice media, were maintained for 8 weeks in glasshouses, with temperature ranging from 15° C. (night) to 25° C. (day), and a natural photo-period. Plants were watered twice daily for 3 min intervals using drip-feed irrigation. The media contained a complex mix of fertilisers (2 kg/m³ dolomite, 1 kg/m³ gypsum, 1 kg/m³ hydraflo, 2 kg/m³ lime, 5 kg/m³ Osmocote Plus, 1.5 kg/m³ Osmoform Pre-mix, 1 kg/m³ Super). Flowers, fruit and secondary shoots were removed throughout the course of the experiments, as were growing tips once the plants had reached an adequate size (11+true leaves). Squash plants were trained up taut strings suspended from the glasshouse roof.

Plants were randomly assigned to treatment groups (8 replicates per group) with one replicate plant from each treatment being randomly positioned on a separate table (block) in the glasshouse.

Treatment applications were at 7-day intervals and involved spraying all leaves to run-off (approximately 5 ml per leaf) using hand-held mister-bottles. The first two spray applications to disease-free plants commenced 7 and 2 days before artificial inoculation, when the plants had at least 8 true leaves (i.e. were 5-6 weeks old), with the third application 2 days after inoculation, and five weekly applications thereafter. All milk ingredients tested were supplied by NZMP (NZ) Ltd, and solutions of these ingredients were prepared the day before application and stored overnight at 4° C.

The first 2 true leaves on each plant were artificially inoculated with PM conidia from the cucurbit PM pathogen *Sphaerotheca fuliginea*. These were obtained from naturally infected glasshouse-grown squash plants. Spores from a detached source leaf were tapped onto the adaxial surface of each true leaf that was to be inoculated. Spores were applied in the same manner to Petri dishes with a known surface area (56.75 cm²) and volume (10 ml) of sterile water containing 0.01% (v/v) Tween 20. Following 15 replicate counts of the Petri dishes, using a Hausser Scientific hemacytometer, it was possible to ascertain that the inoculation process applied $2.7 \times 10^3 \pm 4.7 \times 10^2$ spores/cm² (mean±standard error).

All remaining leaves on each plant were left to develop infection naturally.

Disease severity on true leaves 3-8 was rated fortnightly using percent leaf area infection diagrams (see FIG. 1) and a disease rating scale described by Spencer (9) and shown in Table 1:

TABLE 1

Powdery Mildew leaf disease rating scale from Spencer (9).

| Rating | Percent Leaf Area Infected |
|---|---|
| 0 | no infection |
| 1 | 0-1% infection |
| 2 | 2-5% infection |
| 3 | 6-20% infection |
| 4 | 21-40% infection |
| 5 | >40% infection |
| 6 | 100% infection |

The first assessment was made 2 weeks after the initial treatment application, and then at 4 and 6 weeks. These data were analysed as a repeated measures design (RMD) to determine the treatment effect on disease severity over time. Treatment differences at 6 weeks only were also assessed as a randomised block design (RBD), by analysis of variance (ANOVA), with means separation by Fisher's Least Significant Difference (LSD) ($P<0.05$), using SAS software, version 8.01 TS (SAS Institute, Cary, N.C.).

Qualitative assessments of leaf health/condition were made at the same time as disease severity assessments, using the arbitrary scale described below.

TABLE 2

Arbitrary scale used to describe leaf condition for Trial 1.

| Rating | Leaf Condition |
|---|---|
| A | Perfect condition - no abiotic or biotic blemishes. |
| B | Small blemishes e.g. chlorotic patches, rubbing, insect damage |
| C | Severe/advanced chlorosis, necrosis or leaf distortion |
| D | Leaf dead |

Note:
a rating of A/B indicates a leaf condition intermediate between states A and B.

Trial 1—Treatments

The treatments used are summarised in Table 3.

TABLE 3

Trial 1 treatments.

| Treatment | Code |
|---|---|
| 1) Sulphur fungicide - Kumulus DF ™ (BASF, Germany) (3 g/L) | [sulphur] |
| 2) AMF (30 g/L) + HV40 ™ (4 g/L) (Danisco, Brabrand, Denmark) | [AMF] |
| 3) AMF + HV40 + Grindox 122 ™ (Danisco, Brabrand, Denmark) (1 g/L) | [AMF + antiox] |
| 4) Whole milk (30 g/L) + almond oil (10 ml/L of 7.5% stock solution) | [milk + AO] |
| 5) Whole milk (30 g/L) | [milk] |
| 6) Alaco ™ cream powder 55 (30 g/L) (NZMP (NZ) Ltd) | [cream 55] |

AMF treatments were prepared by by dissolving HV40™ (4 g/L) emulsifier in hot (70° C.) water and adding AMF, followed by blending for 30-60 s. The solution was cooled to at least 30-40° C. before application. Grindox 122™ is an antioxidant, compatible with fats and oils and required prior dissolution in liquefied AMF (>40° C.). Treatments 1 and 4-6 were produced by adding the components to water and mixing.

Trial 1—Results

The data required a square root (SQRT) transformation to satisfy the assumptions required for ANOVA (normal distribution and homogeneity of variances). The corresponding untransformed values for each data point are given in parentheses in FIGS. 2 and 3.

Figure 2:
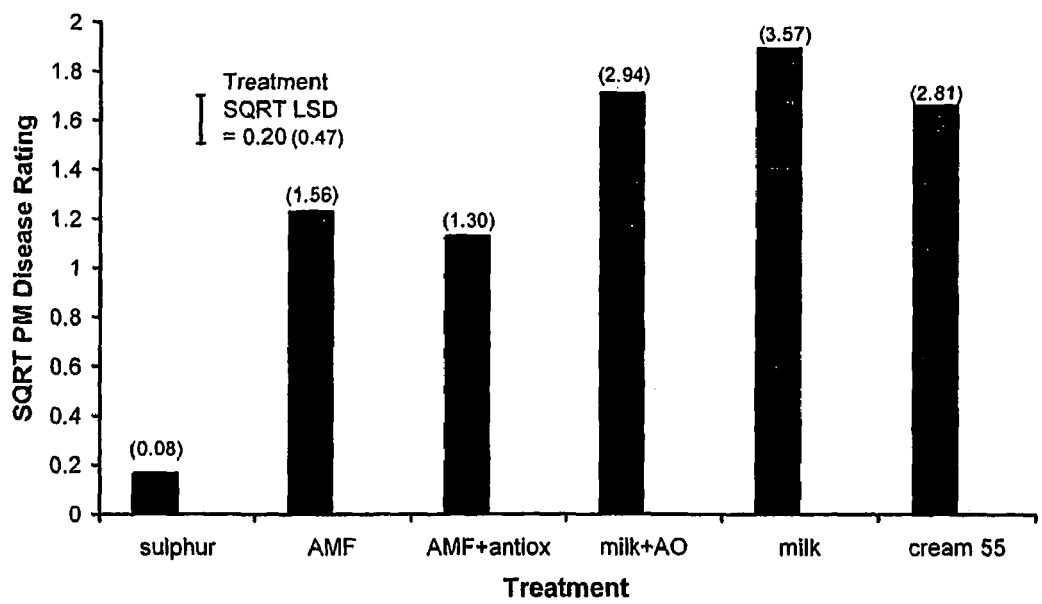
FIG. 2 shows the effects of Trial 1 treatment application on PM disease severity on 'Delica' squash leaves, six weeks after initial treatment application. The data required a square root (SQRT) transformation to satisfy the assumptions required for ANOVA (normal distribution and homogeneity of variances.) The corresponding untransformed values for each data point are given in parentheses.

FIG. 2 shows the effects of Table 3 treatments on PM disease severity on non-inoculated 'Delica' squash leaves, six weeks after initial treatment application.

Whitefly proliferated in the glasshouse during this trial, leading to the co-appearance of sooty mould. Qualitative observations on the degree of sooty mould present in each treatment were made during PM disease assessments.

Sooty mould was abundant in all treatments except sulphur, AMF and AMF+antiox. Sooty mould incidence was mild to non-existent on AMF-treated plants and was most severe for the whole milk and cream 55 treatments.

Six weeks after the initial treatment application, squash plants sprayed with the sulphur, AMF, AMF+antioxidant, and milk+AO treatments had a median leaf heath rating of B, plants sprayed with milk had a B/C rating, and those sprayed with cream 55 had a C rating.

Figure 3:
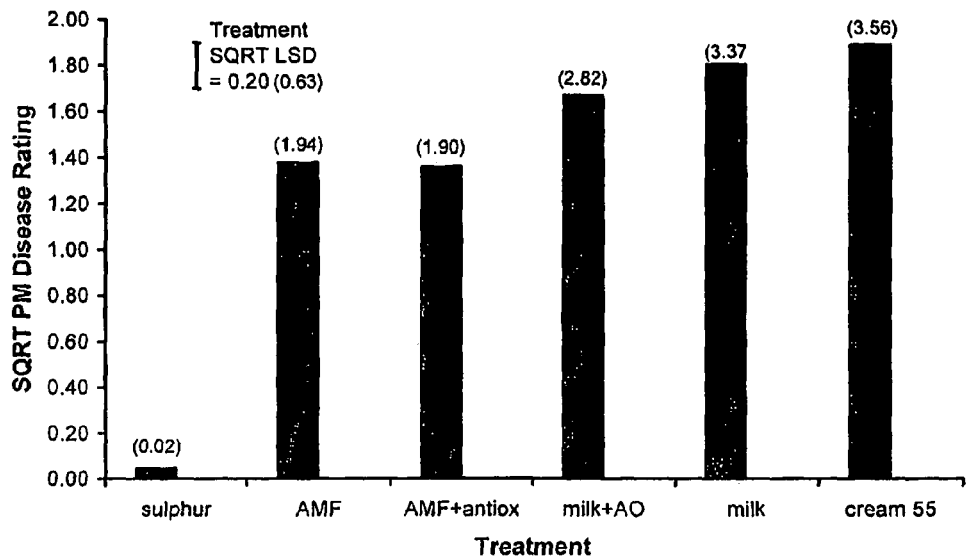
FIG. 3 shows the effects of Trial 1 treatment application on PM disease severity on 'Black Jack' zucchini leaves, six weeks after initial treatment application. ANOVA analysis necessitated a square root (SQRT) data transformation. The corresponding untransformed values for each data point are given in parentheses.

FIG. 3 shows the effects of treatment application on PM disease severity on non-inoculated 'Black Jack' zucchini leaves, six weeks after initial treatment application.

Whitefly and sooty mould were present as described for the squash plants.

Median leaf health ratings for the zucchini plants were B for the sulphur, AMF, AMF+antiox, and milk+AO treatments, and C for the whole milk, and cream 55 treatments.

Trials 2 and 3—General Materials and Methods

Squash (*Cucurbita maxima*) cv 'Delica' were raised and the first true leaf on each plant was artificially inoculated as in Trial 1.

Treatment applications were normally at 7-day intervals (although 14 and 21 day intervals were also used in Trial 3) and involved spraying all leaves to run-off (approximately 5 ml per leaf) using hand-held mister-bottles. The first application commenced 3-4 days after artificial inoculation (except for elicitor treatments in Trial 3), when the non-inoculated leaves on plants were still largely disease-free, and plants had up to 8 true leaves (i.e. were 5-6 weeks old).

All milk ingredients tested were supplied by NZMP (NZ) Ltd, and solutions of these ingredients were prepared the day before application and stored overnight at 4° C.

Disease severity on true leaves 1-8 was rated weekly or fortnightly as discussed above.

Data were analysed as a repeated measures design (RMD) to determine the treatment effect on disease severity over time. Treatment differences at final disease assessment were also assessed as a randomised block design (RBD), by analysis of variance (ANOVA), with means separation by Fisher's Least Significant Difference (LSD) ($P<0.05$), using SAS software, version 8.01 TS (SAS Institute, Cary, N.C.).

Qualitative assessments of leaf health/condition were made at the same time as disease severity assessments, using the arbitrary scale described below.

TABLE 4

Arbitrary scale used to describe leaf condition for Trials 2 and 3.

| Rating | Leaf Condition |
| --- | --- |
| A | Perfect condition - no abiotic or biotic blemishes. |
| B | Minor imperfections, not exceeding a 5 mm2 area. |
| C | Small blemishes 5-10 mm2, e.g. chlorotic spots, rubbing |
| D | Necrotic/chlorotic patches (coalesced spots), leaf distortion |
| E | Severe/advanced chlorosis, necrosis or leaf distortion |
| F | More than 20% of the leaf area is dead |
| G | Leaf dead |

Results for non-inoculated (naturally infected) and inoculated (artificially inoculated) leaves are presented separately. The ability of a treatment to control PM infection was tested for by comparing final levels of infection (after 6 weeks of treatment application) against original infection levels.

Trial 2—Main Treatments

A randomised block design was used comprising 8 blocks (tables in the glasshouse) and 15 treatments (including water sprayed and fungicide treated control plants), with one replicate plant per treatment per block. Treatments were first applied 4 days after artificial inoculation of the first true leaf, and weekly thereafter. There were 6 treatment applications in total.

The treatments used are summarised in Table 5.

TABLE 5

Trial 2 main treatments.

| Treatment | Code |
| --- | --- |
| 1) Kumulus ™ DF (3 g/L) fungicide | [Kumulus] |
| 2) Water | [H2O] |
| 3) AMF (30 g/L) + Alanate 191 ™ (15 g/L) emulsifier + Grindox 122 ™ (1 g/L) antioxidant | [AMF + 191] |
| 4) AMF (30 g/L) + DATEM (8 g/L) emulsifier + Grindox 122 ™ (1 g/L) antioxidant | [AMF + Dat] |
| 5) Synertrol (5 ml/L) spray oil | [Synertrol] |
| 6) Fish oil (20 ml/L) | [Fish] |
| 7) Soya oil (20 ml/L) + DATEM (8 g/L) emulsifier + Grindox 122 ™ (1 g/L) antioxidant | [Soya + Dat] |
| 8) Coconut fat (20 g/L) + DATEM (8 g/L) emulsifier + Grindox 122 ™ (1 g/L) antioxidant | [Coc + Dat] |
| 9) Olive oil (20 ml/L) + DATEM (8 g/L) emulsifier + Grindox 122 ™ (1 g/L) antioxidant | [Oli + Dat] |
| 10) AMF (30 g/L) + DATEM (8 g/L)1 emulsifier + Fish oil (20 ml/L) | [AMF + Dat + Fish] |

TABLE 5-continued

Trial 2 main treatments.

| Treatment | Code |
|---|---|
| 11) AMF (30 g/L) + DATEM (8 g/L)1 emulsifier + Synertrol (5 ml/L) spray oil | [AMF + Dat + Syn] |
| 12) AMF (30 g/L) + DATEM (8 g/L) emulsifier + Coconut fat (2% w/v) | [AMF + Dat + Coc] |
| 13) AMF (30 g/L) + Alanate 191 ™ (15 g/L) emulsifier + Grindox 122 ™ (1 g/L) antioxidant + Natamax ™ (20 mg/L) preservative | [AMF + 191 + Natamax] |
| 14) Buttermilk powder (30 g/L) | [Buttermilk] |
| 15) Alaco ™ cream powder 70 (30 g/L) | [Cream70] |

Treatments were sourced as follows: Kumulus™ DF (BASF, Germany); AMF and Alanate 191™ (NZMP Ltd); Grindox 122™ antioxidant and DATEM Panodan™ AL 10 emulsifier (Danisco Ltd, Brabrand, Denmark); Synertrol Horti Oil (Organic Crop Protectants, NSW, Australia); Fish oil—Bio-Sea™ (SeaLord Group Ltd, Nelson, New Zealand); Soya oil (Amco brand, Goodman Fielder NZ Ltd, Auckland, NZ); coconut fat (Punja and Sons Ltd., Latutoka, Fiji); olive oil (Rizzzoli brand, Italy); Natamax™ (Danisco Ltd, Brabrand, Denmark); and Alaco™ cream powder 70 (NZMP (NZ) Ltd).

Trial 2—Main Treatment Results—Randomised Block Design

Figure 4:
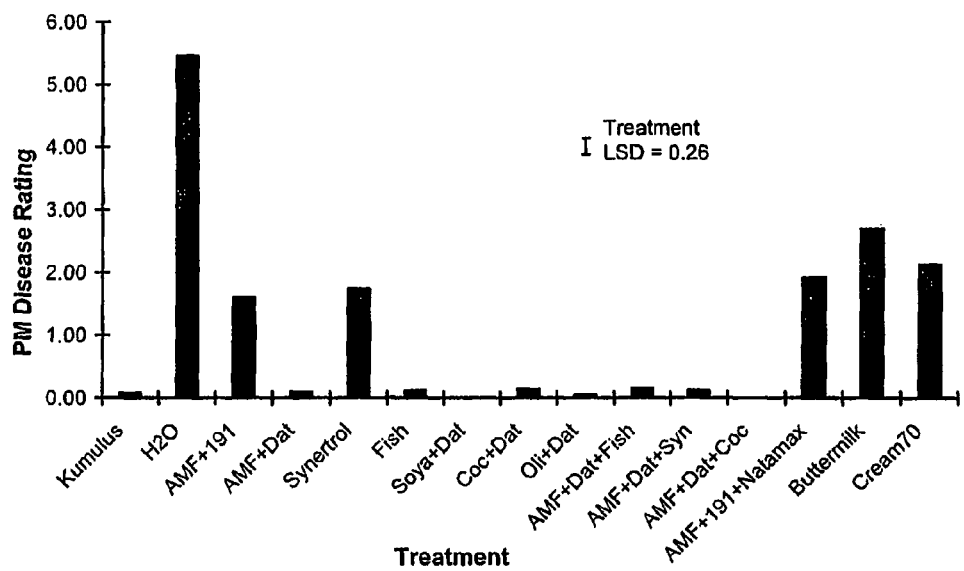
FIG. 4 shows the effects of the Trial 2 Main Treatments on PM disease severity on non-inoculated (naturally infected) 'Delica' squash leaves after six weeks of treatment application.

FIG. 4 shows the effects of the Trial 2 Main Treatments on PM disease severity on non-inoculated leaves after six weeks of treatment application.

"AMF+Dat+Coc", "Soya+Dat", "Oli+Dat", "Kumulus", "AMF+Dat", "Fish", "AMF+Dat+Syn", "Coc+Dat" and "AMF+Dat+Fish" were the most effective treatments in preventing PM infection. All these treatments were equally efficacious, limiting infections to less than 1% of the leaf surface area (PM disease rating <1).

"AMF+191", "Synertrol" and "AMF+191+Natamax" produced intermediate levels of infection (1-5% of the leaf surface area).

"H2O" was the worst treatment, followed by "Buttermilk", and then by "Cream 70".

Leaf health ratings were assessed using the criteria described in Table 4 and are recorded in Table 6. Each value presented in Table 6 is a median value rather than an arithmetic mean.

TABLE 6

Leaf health ratings of non-inoculated leaves 6 weeks of treatment application.

| | Treatment Code | Leaf Health Rating |
|---|---|---|
| 1) | Kumulus | B |
| 2) | H2O | E |
| 3) | AMF + 191 | D |
| 4) | AMF + Dat | G |
| 5) | Synertrol | C |
| 6) | Fish | E |
| 7) | Soya + Dat | B |
| 8) | Coc + Dat | C |
| 9) | Oli + Dat | B |
| 10) | AMF + Dat + Fish | F |
| 11) | AMF + Dat + Syn | F |
| 12) | AMF + Dat + Coc | G |
| 13) | AMF + 191 + Natamax | D |
| 14) | Buttermilk | C |
| 15) | Cream70 | C |

Trial 2—Main Treatment Results—Repeated Measures Design

With assessment of treatment effect over time (2, 4 and 6 week data), highly significant treatment differences in the PM disease ratings were detectable after just 2 weeks of treatment application (p<0.0001, Table 7). Natural infections increased significantly over time for all treatments except "Kumulus", "AMF+Dat", "Fish", "Soya+Dat", "Coc+Dat", "Oli+Dat", "AMF+Dat+Fish", "AMF+Dat+Syn" and "AMF+Dat+Coc", where PM disease ratings remained the same over time or decreased, due to elimination of infections in the latter case.

For inoculated leaves, disease severity was greater than in naturally infected leaves because of artificial introduction of the pathogen before the first treatment application (compare Tables 7 and 8).

TABLE 7

The effects of Trial 2 main treatments on PM disease severity on non-inoculated 'Delica' squash leaves over time.

| | PM Disease Rating | | |
|---|---|---|---|
| Treatment | 2 wks | 4 wks | 6 wks |
| Kumulus | 0.21 | 0.14 | 0.09 |
| H20 | 0.88 | 2.86 | 5.46 |
| AMF + 191 | 0.50 | 0.82 | 1.61 |
| AMF + Dat | 0.04 | 0.13 | 0.11 |
| Synertrol | 0.24 | 0.90 | 1.75 |
| Fish | 0.17 | 0.14 | 0.13 |
| Soya + Dat | 0.00 | 0.00 | 0.02 |
| Coc + Dat | 0.00 | 0.04 | 0.15 |
| Oli + Dat | 0.03 | 0.07 | 0.06 |
| AMF + Dat + Fish | 0.14 | 0.02 | 0.16 |
| AMF + Dat + Syn | 0.27 | 0.02 | 0.13 |
| AMF + Dat + Coc | 0.00 | 0.05 | 0.00 |
| AMF + 191 + Natamax | 0.58 | 1.09 | 1.93 |
| Buttermilk | 0.75 | 1.46 | 2.71 |
| Cream 70 | 0.61 | 1.61 | 2.14 |

Time LSD = 0.19

TABLE 8

The effects of Trial 2 main treatments on PM disease severity on inoculated 'Delica' squash leaves over time.

| | PM Disease Rating | | |
|---|---|---|---|
| Treatment | 2 wks | 4 wks | 6 wks |
| Kumulus | 3.12 | 3.50 | 3.88 |
| H20 | 5.00 | 5.25 | 5.63 |
| AMF + 191 | 3.75 | 3.13 | 2.75 |
| AMF + Dat | 0.63 | 1.50 | 0.00 |
| Synertrol | 3.13 | 3.88 | 4.13 |
| Fish | 2.13 | 1.63 | 1.88 |

TABLE 8-continued

The effects of Trial 2 main treatments on PM disease severity on inoculated 'Delica' squash leaves over time.

| Treatment | PM Disease Rating | | |
|---|---|---|---|
| | 2 wks | 4 wks | 6 wks |
| Soya + Dat | 0.13 | 0.38 | 1.50 |
| Coc + Dat | 1.38 | 1.75 | 2.25 |
| Oli + Dat | 0.88 | 1.50 | 2.43 |
| AMF + Dat + Fish | 3.63 | 2.38 | 3.40 |
| AMF + Dat + Syn | 3.38 | 2.00 | 3.33 |
| AMF + Dat + Coc | 0.25 | 1.71 | 2.00 |
| AMF + 191 + Natamax | 4.00 | 3.63 | 3.38 |
| Buttermilk | 4.63 | 4.63 | 5.13 |
| Cream 70 | 4.38 | 5.13 | 5.57 |

Time LSD = 0.66

Figure 5:
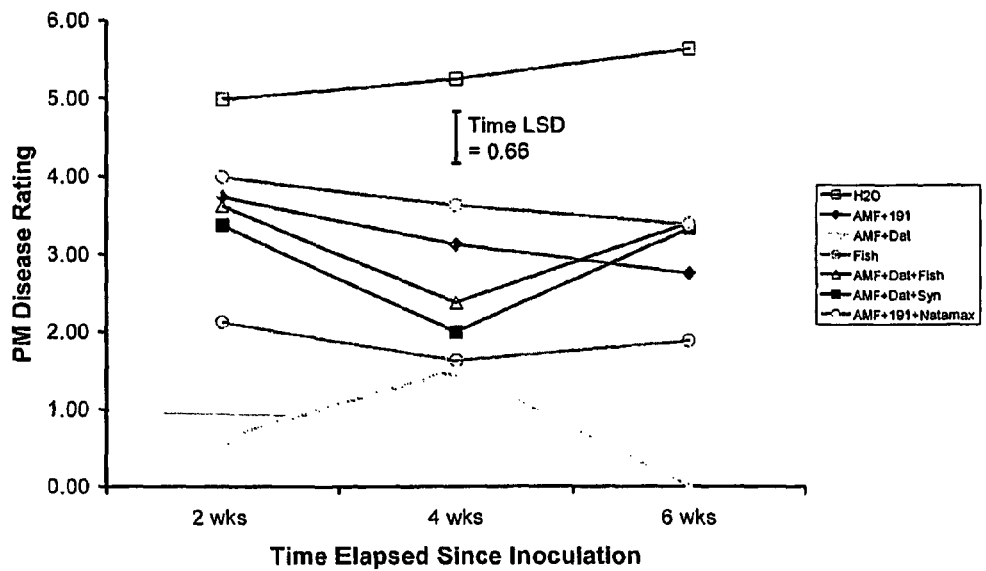
FIG. 5 shows activity of some of the Trial 2 Main Treatments over time on existing PM infections on inoculated 'Delica' squash leaves.

As shown in FIG. 5, decreases in PM disease rating over time were associated with several treatments, namely "AMF+191", "AMF+Dat", "Fish", "AMF+Dat+Fish", "AMF+Dat+Syn" and "AMF+Dat+Natamax".

Trial 2—Additional Treatments

Four additional treatments were also conducted as summarised in Table 9.

TABLE 9

Trial 2 additional treatments.

| Treatment | Code |
|---|---|
| 21) Alanate 191 ™ (30 g/L), dissolved in water at ambient temperature | [191-cold] |
| 22) Alanate 191 ™ (15 g/L), dissolved in water at 70° C. | [191-hot] |
| 23) Grindsted ™ Mono-Di HV40 (4 g/L) emulsifier (Danisco, Ltd, Denmark) | [HV40] |
| 24) DATEM (8 g/L) emulsifier | [DATEM] |

There were two replicate plants per treatment and both replicate plants were on the same table. All plants were naturally infected at the start of this experiment, so the first true leaves were not artificially inoculated. The first disease assessment coincided with the first treatment application and weekly thereafter for a further four treatment applications.

Trial 2—Additional Treatment Results

For the additional treatments in Trial 2, all plants were naturally infected at the time of the first treatment application so there was no need for artificial inoculation. Disease assessments were made at 0, 1, 2, 3 and 4 weeks after the first treatment application, as shown in Table 10.

TABLE 10

The effects of the Trial 2 additional treatments on PM disease severity on non-inoculated 'Delica' squash leaves over time.

| Treatment | PM Disease Rating | | | | |
|---|---|---|---|---|---|
| | 0 wks | 1 wk | 2 wks | 3 wks | 4 wks |
| 191-Cold | 2.43 | 2.57 | 3.57 | 5.08 | 5.36 |
| 191-Hot | 1.57 | 2.36 | 2.79 | 5.07 | 5.43 |
| HV40 | 1.87 | 2.23 | 3.29 | 4.66 | 5.21 |
| DATEM | 1.57 | 1.86 | 2.36 | 3.29 | 3.63 |

Time LSD = 0.47

Trial 3—Main Treatments

The treatments used are summarised in Table 11. Eight replicate squash plants per treatment (1 replicate per block) were assessed.

TABLE 11

Trial 3 main treatments.

| Treatment | Code |
|---|---|
| 1) Water | [H2O] |
| 2) Kumulus ™ DF (3 g/L) fungicide | [Kumulus] |
| 3) AMF (14 g/L) + DATEM (5 g/L) emulsifier + Grindox 122 ™ (1 g/L) antioxidant | [1.4AMF + Dat] |
| 4) AMF (7 g/L) + DATEM (5 g/L) emulsifier + Grindox 122 ™ (1 g/L) antioxidant | [0.7AMF + Dat] |
| 5) AMF (14 g/L) + DATEM (5 g/L) emulsifier + Grindox 122 ™ (1 g/L) antioxidant, applied once per fortnight | [1.4AMF + Dat/2 wk] |
| 6) AMF (14 g/L) + DATEM (5 g/L) emulsifier + Grindox 122 ™ (1 g/L) antioxidant, applied once every three weeks | [1.4AMF + Dat/3 wk] |
| 7) AMF (28 g/L) + Xanthan gum (1 g/L) stabiliser + Palsgaard 7463 (1 g/L) emulsifier + Grindox 122 ™ antioxidant (1 g/L) | [2.8AMF + X/Ps] |
| 8) AMF (14 g/L) + Xanthan gum (1 g/L) stabiliser + Palsgaard 7463 (1 g/L) emulsifier + Grindox 122 ™ (1 g/L) antioxidant | [1.4AMF + X/Ps] |
| 9) AMF (14 g/L) + Xanthan gum (1 g/L) stabiliser + Palsgaard 7463 (1 g/L) emulsifier + Grindox 122 ™ (1 g/L) antioxidant, applied once every three weeks | [1.4AMF + X/Ps/3 wk] |
| 10) AMF (7 g/L) + Xanthan gum (1 g/L) stabiliser + Palsgaard 7463 (1 g/L) emulsifier + Grindox 122 ™ (1 g/L) antioxidant | [0.7AMF + X/Ps] |
| 11) AMF (7 g/L) + Soya oil (7 ml/L) + DATEM (5 g/L) emulsifier + Grindox 122 ™ (1 g/L) antioxidant | [AMF + Soy + Dat] |
| 12) AMF (7 g/L) + Coconut fat (7 g/L) + DATEM (5 g/L) emulsifier + Grindox 122 ™ (1 g/L) antioxidant | [AMF + Coc + Dat] |
| 13) Bion ™ (50 ppm) elicitor + AMF (14 g/L) + DATEM (5 g/L) emulsifier + Grindox 122 ™ (1 g/L) antioxidant | [BTH + AMF + Dat] |

TABLE 11-continued

Trial 3 main treatments.

| Treatment | Code |
| --- | --- |
| 14) BABA (25 ml/L of a 10 mg/ml stock solution) elicitor + AMF (14 g/L) + DATEM (5 g/L) emulsifier + Grindox 122 ™ (1 g/L) antioxidant | [BABA + AMF + Dat] |
| 15) Chitosan (20 ml/L of a 10 mg/ml stock solution) elicitor + AMF (14 g/L) + DATEM (5 g/L) emulsifier + Grindox 122 ™ (1 g/L) antioxidant | [Chit + AMF + Dat] |
| 16) Caprylic acid (10 g/L) + Capric acid (10 g/L) + Monolaurin (5 g/L) | [Capry + CA + LA] |
| 17) Poem J-2021 (1.25 g/L) | [1.25 J-2021] |
| 18) Poem J-2021 (5 g/L) | [5 J-2021] |
| 19) Capric acid (0.34 g/L) + Lauric acid (0.40 g/L) | [CA + LA] |
| 20) Linoleic acid (0.14 g/L) | [Linol] |

Treatments were sourced as follows: Xanthan gum and Palsgaard 7463 (Hawkins Watts Ltd, Auckland, NZ); Bion (Syngenta, N.C., USA); BABA (DL-3-amino-n-butanoic acid, β-aminobutyric acid) (Sigma-Aldrich, NSW, Australia); Chitosan (Sigma-Aldrich, NSW, Australia); Caprylic acid, capric acid and linoleic acid (Sigma-Aldrich, NSW, Australia); Monolaurin (Danisco Ltd, Brabrand, Denmark); and Poem J-2021 (Riken Vitamin Co. Ltd, Tokyo, Japan).

The first true leaf of each plant was artificially inoculated with PM, while all other leaves on the plant were allowed to infect naturally. Elicitors (treatments 13-15) were first applied 5 days before artificial inoculation, to allow time for induction of host defences prior to advent of the PM fungus, and every three weeks thereafter. Repeat applications of Bion™ caused phyto-toxicity so this elicitor was only included in treatment 13 at the first application, and subsequent applications comprised just AMF+DATEM+Grindox 122. All other treatments were first applied 3 days after artificial inoculation and at weekly (treatments 1-4, 7-8, 10-12, 16-20), fortnightly (treatment 5), or 3 weekly intervals (treatments 6 and 9) thereafter.

The effect of selected treatments on the germination of three other important horticultural fungi, *Bouytis cinerea* (causal agent of grey mould on grapes, kiwifruit, tomatoes, strawberries, etc), *Monilinia fructicola* (causal agent of brown rot on stonefruit), and *Cladosporium cladosporiodes* (one of the fungi that can cause sooty mould) were also assessed using the 96-multiwell assay of Wilson et al (10).

Trial 3—Main Treatment Results—Randomised Block Design

Figure 6:
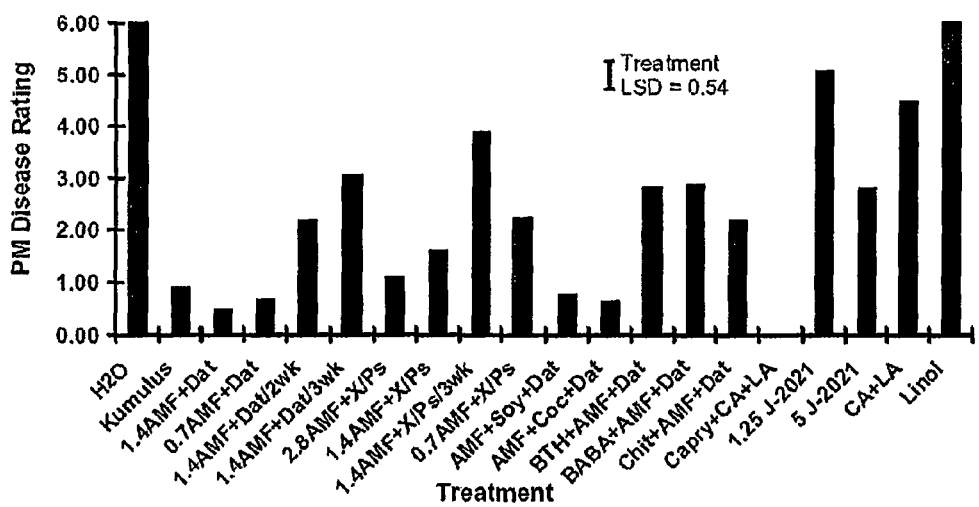
FIG. 6 shows the effects of the Trial 3 Main Treatments on PM disease severity on non-inoculated 'Delica' squash leaves, after seven weeks of treatment application.

FIG. 6 shows the effects of the Trial 3 Main Treatments on disease severity in non-inoculated plants after 7 weeks of treatment. FIG. 6 does, not present any value for the "Capry+CA+LA" treatment because all non-inoculated leaves were dead due to severe phyto-toxicity.

Leaf health ratings of non-inoculated leaves from Trial 3 after 7 weeks of treatment application are shown in Table 12. Leaf health ratings were assessed using the criteria described in Table 4. Each value presented in Table 12 is a median value rather than an arithmetic mean.

TABLE 12

Leaf health ratings for Trial 3 main treatments.

| | Abbreviated Treatment Code | Leaf Health Rating |
| --- | --- | --- |
| 1) | H2O | F |
| 2) | Kumulus | E |
| 3) | 1.4AMF + Dat | B |
| 4) | 0.7AMF + Dat | B |
| 5) | 1.4AMF + Dat/2 wk | D |
| 6) | 1.4AMF + Dat/3 wk | E |
| 7) | 2.8AMF + X/Ps | F |
| 8) | 1.4AMF + X/Ps | F |
| 9) | 1.4AMF + X/Ps/3 wk | E |
| 10) | 0.7AMF + X/Ps | E |
| 11) | AMF + Soy + Dat | E |
| 12) | AMF + Coc + Dat | C |
| 13) | BTH + AMF + Dat | E |
| 14) | BABA + AMF + Dat | E |
| 15) | Chit + AMF + Dat | E |
| 16) | Capry + CA + LA | G |
| 17) | 1.25 J-2021 | E |
| 18) | 5 J-2021 | E |
| 19) | CA + LA | E |
| 20) | Linol | F |

Trial 3—Main Treatment Results—Repeated Measures Design Treatment effect over time at 0, 2, 4, 6 and 7 weeks was assessed.

At the start of this trial (0 weeks after inoculation of the first true leaf), natural PM infections on the non-inoculated leaves (leaves 2-8) covered less than 1% of the leaf surface area, and there were no significant treatment differences at this stage except for plants from the three elicitor treatments containing BTH, BABA and Chitosan (Table 13). These elicited plants were virtually infection-free at 0 weeks, and were the only plants to receive a spray application 5 days before artificial inoculation (Table 13). Five days before artificial inoculation, all plants i.e. not only those treated with elicitors, were largely free of natural infection. Treatment effects were highly significant ($p<0.0001$) just two weeks after artificial inoculation, with a rapid breakdown in protective activity occurring in the "H2O", "BTH+AMF+Dat", "BABA+AMF+Dat", "1.25 J-2021", "CA+LA" and "Linol" treatments (Table 13). After 4 weeks of treatment application, all non-inoculated leaves had died in the "Capry+CA+LA" treatment so disease assessments were not possible after this time. For most treatments, the greatest increases in natural infections took place between 4 and 6 weeks, but disease severity in the "Kumulus", "1.4AMF+Dat", "0.7AMF+Dat", "AMF+Soy+Dat" and "AMF+Coc+Dat" treatments remained at or below the 0 week level throughout the course of the experiment. (Table 13).

TABLE 13

The effects of Trial 3 main treatments on PM disease severity on non-inoculated 'Delica' squash leaves over time.

| | PM Disease Rating | | | | |
|---|---|---|---|---|---|
| Treatment | 0 wks | 2 wks | 4 wks | 6 wks | 7 wks |
| H20 | 0.62 | 2.94 | 5.61 | 5.88 | 6.00 |
| Kumulus | 0.70 | 0.79 | 0.79 | 0.94 | 0.90 |
| 1.4 AMF + Dat | 0.57 | 0.31 | 0.46 | 0.53 | 0.48 |
| 0.7 AMF + Dat | 0.54 | 0.42 | 0.63 | 0.52 | 0.67 |
| 1.4 AMF + Dat/2 wk | 0.65 | 0.69 | 1.48 | 1.86 | 2.18 |
| 1.4 AMF + Dat/3 wk | 0.63 | 0.60 | 2.27 | 2.98 | 3.08 |
| 2.8 AMF + X/Ps | 0.65 | 0.63 | 0.86 | 1.19 | 1.07 |
| 1.4 AMF + X/Ps | 0.63 | 0.90 | 1.25 | 1.28 | 1.63 |
| 1.4 AMF + X/Ps/3 wk | 0.63 | 1.31 | 3.40 | 3.88 | 3.90 |
| 0.7 AMF + X/Ps | 0.65 | 1.27 | 1.88 | 2.08 | 2.25 |
| AMF + Soy + Dat | 0.56 | 0.54 | 0.49 | 0.71 | 0.77 |
| AMF + Coc + Dat | 0.65 | 0.52 | 0.46 | 0.52 | 0.65 |
| BTH + AMF + Dat | 0.13 | 1.04 | 2.19 | 2.56 | 2.83 |
| BABA + AMF + Dat | 0.22 | 1.05 | 2.35 | 2.74 | 2.87 |
| Chit + AMF + Dat | 0.23 | 0.63 | 1.65 | 2.06 | 2.20 |
| Capry + CA + LA | 0.62 | 0.00 | 4.00 | —* | —* |
| 1.25 J-2021 | 0.53 | 2.13 | 4.33 | 5.03 | 5.08 |
| 5 J-2021 | 0.62 | 0.81 | 2.10 | 2.67 | 2.81 |
| CA + LA | 0.74 | 2.23 | 3.61 | 4.34 | 4.49 |
| Linol | 0.63 | 2.77 | 5.56 | 6.00 | 6.00 |

Time LSD = 0.34
*Plants were dead from phyto-toxicity

For many of the treatments applied to inoculated leaves, disease severity decreased over the first 4 weeks, relative to infection levels at the start of the experiment (Table 14). However, disease increased steadily throughout the trial on plants sprayed with "H2O", "CA+LA" and "Linol". It was not possible to measure disease rating of leaves receiving the "Capry+CA+LA" treatment from week 2 onwards, because they had died from severe phyto-toxicity.

TABLE 14

The effects of Trial 3 main treatments on PM disease severity on inoculated 'Delica' squash leaves over time.

| | PM Disease Rating | | | | |
|---|---|---|---|---|---|
| Treatment | 0 wks | 2 wks | 4 wks | 6 wks | 7 wks |
| H20 | 3.00 | 5.50 | 6.00 | 6.00 | 6.00 |
| Kumulus | 2.75 | 3.13 | 2.13 | 3.63 | 3.63 |
| 1.4 AMF + Dat | 3.25 | 1.50 | 1.25 | 1.83 | 2.88 |
| 0.7 AMF + Dat | 2.88 | 1.88 | 1.25 | 2.43 | 2.57 |
| 1.4 AMF + Dat/2 wk | 2.75 | 2.13 | 1.63 | 3.13 | 3.43 |
| 1.4 AMF + Dat/3 wk | 2.75 | 1.88 | 1.75 | 2.86 | 3.63 |
| 2.8 AMF + X/Ps | 2.63 | 2.13 | 1.38 | 3.25 | 3.88 |
| 1.4 AMF + X/Ps | 2.75 | 2.50 | 2.00 | 3.13 | 3.38 |
| 1.4 AMF + X/Ps/3 wk | 2.75 | 3.50 | 3.38 | 4.50 | 4.38 |
| 0.7 AMF + X/Ps | 2.75 | 3.50 | 3.00 | 4.00 | 4.50 |
| AMF + Soy + Dat | 2.63 | 1.63 | 1.00 | 2.88 | 2.86 |
| AMF + Coc + Dat | 2.88 | 1.88 | 1.38 | 3.00 | 4.13 |
| BTH + AMF + Dat | 1.88 | 2.88 | 2.29 | 4.71 | 5.00 |
| BABA + AMF + Dat | 1.50 | 3.88 | 2.38 | 4.63 | 4.75 |
| Chit + AMF + Dat | 1.63 | 2.63 | 1.75 | 3.71 | 3.71 |
| Capry + CA + LA | 3.00 | —* | —* | —* | —* |
| 1.25 J-2021 | 3.00 | 4.63 | 4.25 | 5.13 | 5.25 |
| 5 J-2021 | 2.75 | 2.63 | 1.88 | 3.57 | 4.17 |
| CA + LA | 3.25 | 5.00 | 5.13 | 5.57 | 5.71 |
| Linol | 2.63 | 5.25 | 5.88 | 6.00 | 6.00 |

Time LSD = 0.67
*Plants were dead from phyto-toxicity

Trial 3—Additional Treatments
Two additional treatments comprised:

TABLE 15

Trial 3 additional treatments.

| Treatment | Code |
|---|---|
| 21) AMF (7 g/L) + Olive oil (7 ml/L) + DATEM (5 g/L) emulsifier + Grindox 122 ™ (1 g/L) antioxidant | [AMF + Oli + Dat] |
| 22) Di-glycerine-mono-laurate (2.45 g/L) (Danisco Ltd, Brabrand, Denmark) | [DGML] |

Treatments were first applied 3 days after artificial inoculation of leaf 1, and at weekly intervals thereafter. There were 4 replicates per treatment, with two replicates per table per glasshouse.

Trial 3—Additional Treatment Results

Figure 7:
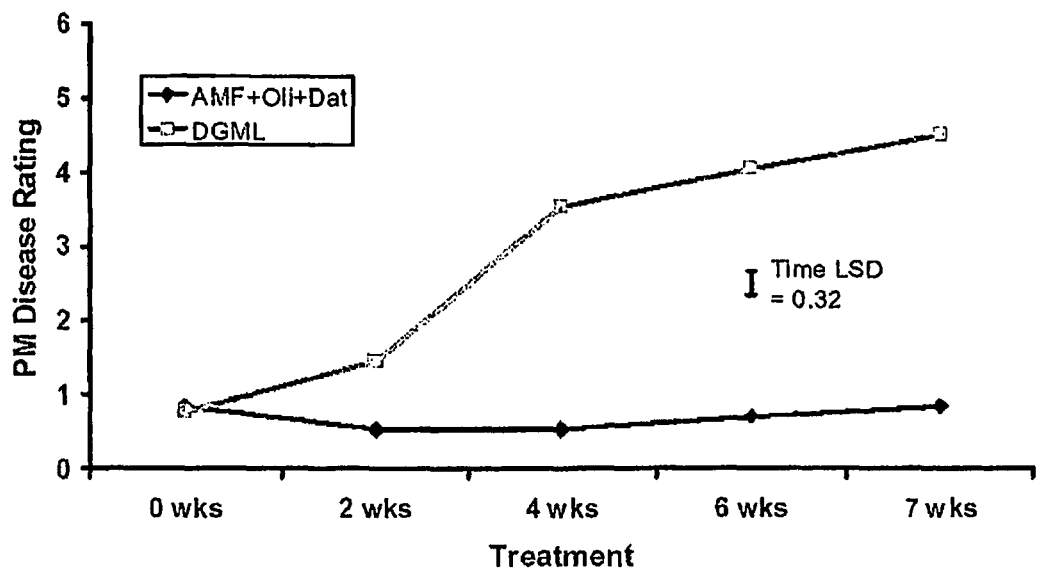
FIG. 7 shows the effects of the Trial 3 Additional Treatments on PM disease severity on non-inoculated 'Delica' squash leaves over time.

Disease severity increased significantly over time on non-inoculated leaves treated with "DGML", but natural infections remained the same as the original levels through the course of the experiment for "AMF+Oli+Dat" (FIG. 7). After 7 weeks, leaf health rating for non-inoculated "DGML" and "AMF+Oli+Dat" leaves were E and D, respectively.

Figure 8:
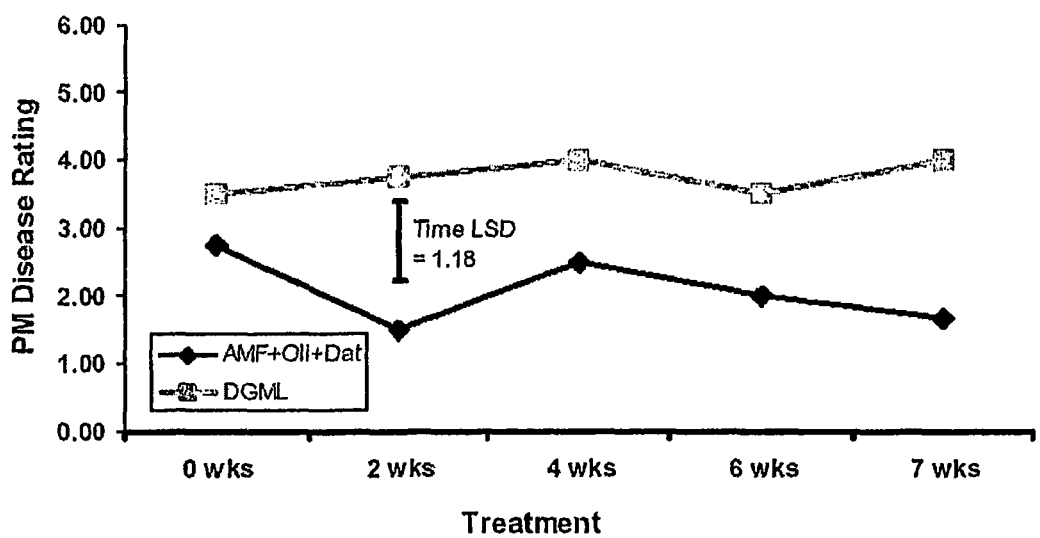
FIG. 8 shows the effects of Trial 3 Additional Treatments on PM disease severity on inoculated 'Delica' squash leaves over time.

The decrease in the PM disease rating from 0 to 2 wks for inoculated leaves in the "AMF+Oli+Dat" treatment was significant (FIG. 8). Health ratings for the first true leaf in both treatments were F/G due to natural senescence.

Trial 3—Main Treatment Results—Fungi Germination

Table 16 compares germination inhibition of *Botrytis cinerea*, *Cladosporium cladosporioides*, and *Monilinia fructicola* spores by Trial 3 treatments, after 24 hours incubation at 19° C.

TABLE 16

Germination inhibition of Botrytis cinerea, *Cladosporum cladosporioides*, and *Monilinia fructicola* spores by Trial 3 treatment preparations, after 24 hours incubation at 19° C.

| Treatment Code | Botrytis | Clado. | Monilinia | Overall Rating |
|---|---|---|---|---|
| H20 | — | — | — | 0 |
| Kumulus | ** | *** | **** | 9 |
| 1.4AMF + Dat | *** | **** | **** | 11 |
| 0.7AMF + Dat | *** | **** | ** | 9 |
| 2.8AMF + X/Ps | — | ** | — | 2 |
| 1.4AMF + X/Ps | * | * | — | 2 |
| 0.7AMF + X/Ps | — | — | — | 0 |
| AMF + Soy + Dat | **** | **** | **** | 12 |
| AMF + Coc + Dat | **** | **** | *** | 11 |
| BTH + AMF + Dat | **** | **** | *** | 11 |
| BABA + AMF + Dat | ** | **** | ** | 8 |
| Chit + AMF + Dat | *** | **** | **** | 11 |
| Capry + CA + ML | **** | **** | **** | 12 |
| 1.25 J-2021 | — | * | ** | 3 |
| 5 J-2021 | ** | ** | ** | 6 |
| CA + LA | *** | **** | **** | 11 |
| Linol | — | — | — | 0 |
| AMF + Oli + Dat | *** | **** | *** | 10 |
| DGML | ** | **** | **** | 10 |

Key:
**** No germination (score 4)
*** Slight germination (3)
** Moderate germination (2)
* Germination, less than control (1)
— No activity = germination same as the control (score 0)

The Overall Rating is the sum of all the germination scores for each treatment (maximum possible value: 12 (greatest inhibition); minimum: 0 (no inhibition)).

Trial 4—Stability/Storage

Three AMF emulsions were subjected to an ACVM (Agricultural Compounds and Veterinary Medicines) accelerated storage test to quantify their stability. The accelerated storage test (http://www.nzfsa.govt.nz/acvm/publications/standards-guidelines/chem-pc.pdf—last accessed 11 Jul. 2005, see also 23 ACVM 06/05) comprised storing 3 batches of each product for 2 weeks at 54° C., conditions thought to approximate 2 years storage at ambient temperature. Immediately before and after accelerated storage, peroxide value (PV), p-anisidine value (AV), and free fatty acids (FFA) were measured by AgriQuality New Zealand Ltd, Auckland. These measurements provide an indication of the extent of lipid oxidation that releases flavour compounds responsible for unpleasant odours and flavours. Since analysis of the end products of lipid auto-oxidation is problematic, indicative measures of oxidation are:

Peroxide value measures hydroperoxides, intermediate compounds of lipid oxidation that can be further oxidised to produce powerful aroma compounds.

Anisidine value measures $\alpha/\beta$ unsaturated aldehydes, which are by-products of lipid oxidation Free fatty acids these tend to increase as complex lipids are degraded. Short chain fatty acids also contribute to odours, but are difficult to detect by this assay.

The TOTOX number (AV+(2×PV)) was also calculated for all samples tested. This number provides a single estimate of both intermediate and end products resulting from lipid oxidation. The three emulsions tested are set out in Table 17.

TABLE 17

Treatments subjected to accelerated storage trial.

| Treatment | Code |
| --- | --- |
| 1) AMF (30 g/L) + Alanate 191 ™ (15 g/L) + Grindox 122 ™ (1 g/L) | [AMF + 191] |
| 2) AMF (30 g/L) + DATEM (8 g/L) + Grindox 122 ™ (1 g/L) | [AMF + Dat] |
| 3) AMF (30 g/L) + Xanthan gum (1 g/L) + Palsgaard ™ 7463 (1 g/L) + Grindox 122 ™ (1 g/L) | [AMF + X/Ps] |

Both before and after the accelerated storage trial, all three emulsions remained stable, in that they had not separated out into separate phases or developed any offensive odours. The results of the trial are shown in Table 18.

TABLE 18

Oxidative degradation in milk fat emulsions following an accelerated storage test, as measured by Peroxide Value (PV), p-Anisidine Value (AV), Free Fatty Acids (FFA) and TOTOX.

| Emulsion | PV (meqO$_2$/kg fat$^a$) | AV$^b$ | FFA$^c$ (%) | TOTOX |
| --- | --- | --- | --- | --- |
| Before Storage | | | | |
| AMF + 191 | 5.00 ± 0.00 | 1.83 ± 0.34 | 0.03 ± 0.00 | 11.83 |
| AMF + Dat | 2.93 ± 0.29 | 3.13 ± 0.48 | 0.16 ± 0.00 | 8.99 |
| AMF + X/Ps | 4.47 ± 0.44 | 2.13 ± 0.23 | 0.03 ± 0.00 | 11.07 |
| After Storage | | | | |
| AMF + 191 | 3.67 ± 0.72 | 2.17 ± 0.54 | 0.01 ± 0.00 | 9.51 |
| AMF + Dat | 3.67 ± 0.41 | 5.90 ± 0.29 | 0.43 ± 0.01 | 13.24 |
| AMF + X/Ps | 4.60 ± 0.15 | 2.80 ± 0.10 | 0.03 ± 0.00 | 12.00 |

$^a$milliequivalents of O$_2$ per kg fat
$^b$measured as optical density on a per fat rather than a per sample basis, this value has no units
$^c$measured as percent mass/mass, i.e. g per 100 g of sample Despite the change in TOTOX value for the "AMF+Dat" and "AMF+X/Ps" emulsions any oxidation that occurred was insufficient to cause breakdown of the emulsion, or development of offensive odours.

Trial 5—Materials and Methods

Mature (11 year old) grapevines (*Vitis vinifera*) cv. Chardonnay were allowed to infect naturally. There were five treatments as shown in Table 19. Nine sprays were applied between capfall and harvest as detailed in Table 20, using a motorised, moderate pressure handgun, at an application rate of 500 L/ha during capfall and thereafter at 800 L/ha. The milk fat fungicide was prepared as an emulsifiable concentrate, diluted 35-fold with water immediately prior to use.

*Botrytis cinerea*, sour rot and powdery mildew disease incidences (percentage of bunches/leaves infected) and severities (percentage of leaf/bunch area covered by disease) were assessed using 50 leaves/bunches per plot. Percentage of total fruit crop/leaf canopy infected was calculated as the product of disease incidence and mean severity. PM infections on fruit were assessed at veraison. PM infections on leaves, *B. cinerea* and sour rot infections on fruit and yield (kg fruit/vine) were assessed at harvest. The experiment was analysed as a randomised block design with 4 replicate vines per treatment, with each replicate vine in a separate row (plot). ANOVA and means separation by LSD (P<0.05) were performed using SAS software, version 8.02 (SAS Institute, Cary, N.C.).

Trial 5—Treatments

TABLE 19

Trial 5 treatments.

| Treatment | Abbreviated Treatment Code |
| --- | --- |
| Unsprayed (nil fungicides) | [Unsprayed] |
| Kumulus ® DF (BASF, Germany) (3 g/L) | [Kumulus] |
| Kocide ® 2000 DF (1.5 g/L) | [Kocide] |
| Full fungicides (Shirlan ®, Switch ®, Dithane ® M45 WDG, Captan WG, Teldor ®, Scala ®, and Rovral ® FLO) | [Full Fungic] |
| AMF (7 g/L) + DATEM (5 g/L) emulsifier + Grindox 122 ™ (1 g/L) antioxidant | [AMF + Dat] |

The fungicides, Rovral® FLO and Scala® are produced by Bayer AG, Germany; Captan WG by Crop Care Australasia (Brisbane, Australia); Switch® by Syngenta (Basel, Switzerland); Dithan® M45 WDG by Dow AgroSciences (IN, USA), Shirlan® By Zeneca Ltd (Hertfordshire, UK) and Kocide® 2000 DF by the Griffin Corporation, USA.

TABLE 20

Trial 5 treatment application schedule.

| | Vine Phenology At Time of Spray Application | | | | | | | | |
|---|---|---|---|---|---|---|---|---|---|
| Treatment Code | 5% capfall | 80% capfall | Post-bloom | Berries pea size | Pre-bunch closure | Post bunch closure | Veraison | 4.5 wk pre-vintage | 2.5 wk pre-vinatge |
| Unsprayed | — | — | — | — | — | — | — | — | — |
| Kumulus | 30 g/10 L | 30 g/10 L | 30 g/10 L | 30 g/10 L | 30 g/10 L | 30 g/10 L | 30 g/10 L | — | — |
| Kocide | 15 g/10 L | 15 g/10 L | 15 g/10 L | 15 g/10 L | 15 g/10 L | 15 g/10 L | 15 g/10 L | 15 g/10 L | 15 g/10 L |
| Full Fungic | Shirlan 10 ml/10 L | Switch 8 g/10 L | Dithane 20 g/10 L | Captan 12.5 g/10 L | Teldor 7.5 ml/10 L | Captan 12.5 g/10 L | Scala 20 ml/10 L | Captan 12.5 g/10 L | Rovral 300 ml/10 L |
| | Kumulus 30 g/10 L | Kumulus 30 g/10 L | Kumulus 30 g/10 L | Kumulus 30 g/10 L | Kumulus 30 g/10 L | Kumulus 30 g/10 L | Kumulus 30 g/10 L | — | — |
| AMF + Dat | All applications: AMF (7 g/L) + Datem (5 g/L) + Grindox 122 (1 g/L) | | | | | | | | |

Trial 5—Results

Figure 9:
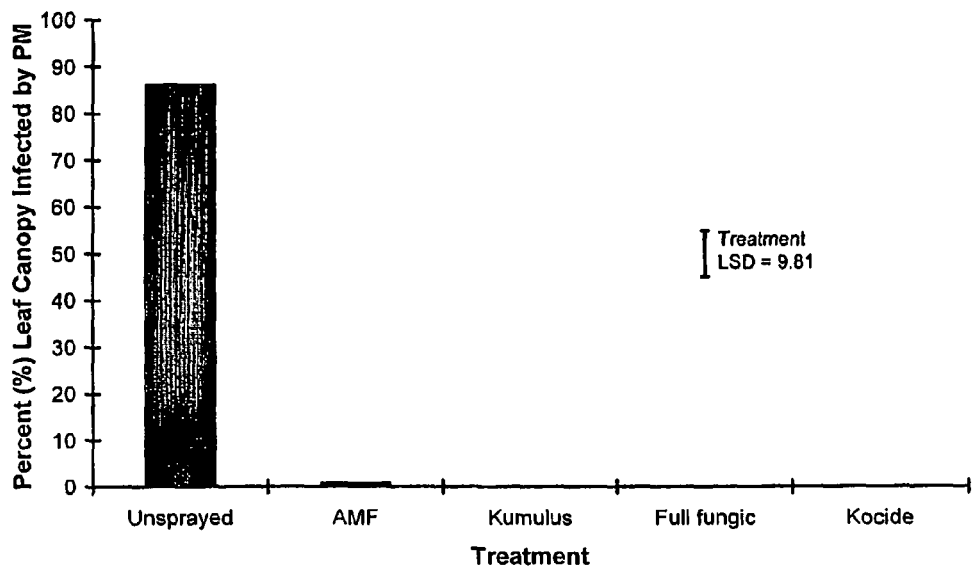
FIG. 9 shows the percentage leaf canopy area of 'Chardonnay' grapevines in Trial 5 infected by PM, assessed after a 4-month spray programme. Fifty leaves per plot were inspected for mildew incidence (percentage leaves infected) and severity (percentage leaf area covered by mildew), with percentage of total canopy infected calculated as the product of disease incidence and mean severity.

"AMF" provided control of PM on grapevine leaves that equaled that of the sulphur ("Kumulus"), copper ("Kocide"), and full fungicide ("Full fungic") spray programmes (FIG. 9). On grape berries, "Kumulus" and "AMF" provided control that was significantly greater than that on "Unsprayed" berries, but not quite as good as that demonstrated by "Kocide" and the "Full fungic" treatments. Table 21 shows the effects of Trial 5 treatments on the percentage of total fruit crop infected by PM, assessed at veraison. Total crop infected was calculated as a product of disease incidence and mean severity, using data collected from fifty randomly selected bunches per vine. Data required a $\log_e$ transformation to satisfy the assumptions of ANOVA (normal distribution and homogeneity of variances). Corresponding untransformed values are provided in parentheses.

TABLE 21

Effect of Trial 5 treatments on the percentage of total fruit crop infected by PM, assessed at veraison.

| Treatment Code | $\log_e$ Mean % Fruit Crop Infected by PM | Means Separation by LSD* |
|---|---|---|
| Unsprayed | 2.21 (9.55) | A |
| Kocide | −0.60 (1.05) | B |
| AMF | −1.92 (0.17) | B |
| Full fungic | −3.36 (0.02) | C |

LSD = 1.38 (2.15)
*Means separated by different letters are significantly different.

The "Full fungic" and "AMF" treatments provided the best control of *B. cinerea*, followed by "Koicde" and "Unsprayed" plants. "Kumulus" use appeared to predispose plants to *B. cinerea* (Table 22). The same treatment trends occurred for sour rots (Table 23), but were not statistically significant.

Table 22 shows the effects of Trial 5 treatments on the percentage of total fruit crop infected by *Botrytis cinerea*, assessed at harvest. Data required a $\log_e$ transformation to satisfy the assumptions of ANOVA (normal distribution and homogeneity of variances). Corresponding untransformed values are provided in parentheses.

TABLE 22

Effect of Trial 5 treatments on the percentage of total fruit crop infected by *Botrytis cinerea*, assessed at harvest.

| Treatment Code | $\log_e$ Mean % Fruit Crop Infected by *B. cinerea* | Means Separation by LSD* |
|---|---|---|
| Kumulus | 1.62 (5.30) | A |
| Unsprayed | −0.14 (1.34) | B |
| Kocide | −0.72 (0.50) | B |
| AMF | −1.92 (0.25) | C |
| Full fungic | −2.13 (0.13) | C |

LSD = 0.93 (1.78)
*Means separated by different letters are significantly different.

Table 23 shows the effects of Trial 5 treatments on the percentage of total fruit crop infected by sour rots, assessed at harvest. Data required a $\log_e$ transformation to satisfy the assumptions of ANOVA (normal distribution and homogeneity of variances). Corresponding untransformed values are provided in parentheses.

TABLE 23

Effect of Trial 5 treatments on the percentage of total fruit crop infected by sour rots, assessed at harvest.

| Treatment Code | $\log_e$ Mean % Fruit Crop Infected by Sour Rots | Means Separation by LSD* |
|---|---|---|
| Kumulus | −1.17 (0.25) | A |
| Unsprayed | −1.20 (0.17) | A |
| Kocide | −1.61 (0.05) | A |
| AMF | −1.97 (0.04) | A |
| Full fungic | −2.67 (0.04) | A |

LSD = 8.74 (0.36)
*Means separated by different letters are significantly different.

Figure 10:
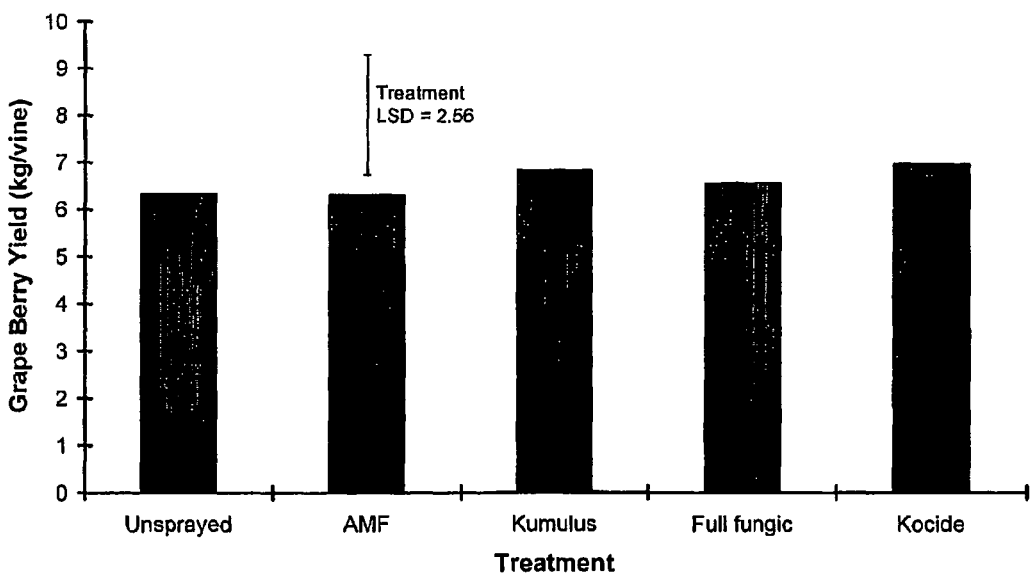
FIG. 10 shows the total 'Chardonnay' grape berry yield (kg) per vine in Trial 5.

None of the treatments had any significant effect on yield (FIG. 10).

Trial 6—Materials and Methods

Figure 11:
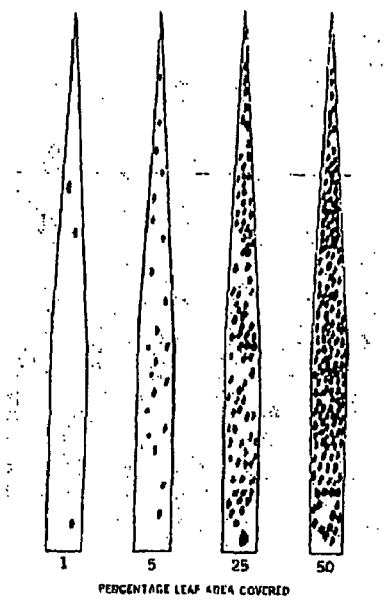
FIG. 11 shows the PM leaf standard area diagrams for use on wheat, from James (11).

Wheat (*Triticum aestivum*) plants, cultivar Endeavour, were sown at a density of four plants per 12 cm diam. pot, with two pots per treatment. Plants were maintained in two blocks (1 pot/treatment/block) in a C.E. room at 20° C. with a 16-hour photoperiod. After one week, the experimental plants were artificially inoculated by brushing them against inoculum wheat plants infected with *Erysiphe graminis* f sp. *tritici* (wheat PM). Treatment application commenced when the plants were two weeks old and at plant growth stage (PGS) 1, as defined by James (11). Leaves were sprayed to run-off using a hand-held spray bottle, with a total of 9 spray applications being made over a course of 7 weeks (2 sprays/week for the first fortnight, and 1 spray/week thereafter). The first disease assessment (designated Time 0) was made immediately before the first treatment application, followed by assessments at two weeks (PGS=3-4), 3 weeks (PGS=4-5), 5 weeks (PGS=8), and 7 weeks (PGS=8-10). Disease severity on the 3 most basal leaves of each plant was assessed using percent leaf area infection diagrams (FIG. 11), and the rating scale shown in Table 24. Disease ratings for the three leaves were averaged to give one value per plant. Since disease assessments were made on different leaves on each assessment date, data from each assessment date was analysed separately, using a nested design, with treatments nested within pots and plants within treatments and pots.

TABLE 24

Wheat PM leaf disease rating scale.

| Rating | Percent Leaf Area Infected |
|---|---|
| 0 | no infection |
| 1 | 1% infection |
| 1.5 | 1-5% infection |
| 2 | 5% infection |
| 2.5 | 5-25% infection |
| 3 | 25% infection |
| 3.5 | 25-50% infection |
| 4 | 50% infection |
| 4.5 | >50% infection |

Trial 6—Treatments
There were 5 treatments as follows:

TABLE 25

Trial 6 treatments.

| Treatment | Treatment Code |
|---|---|
| Unsprayed control - no fungicides | Unsprayed |
| Water control | Water |
| Amistar ® WG fungicide (0.4 g/L) (Syngenta, Basel, Switzerland) | Amistar |
| AMF (7 g/L) + DATEM (5 g/L) + Grindox 122 ™ (1 g/L) | AMF |
| Soybean oil (20 g/L) + DATEM (5 g/L) + Grindox 122 ™ (1 g/L) | Soy |

Trial 6—Results

Only data from the first (Time=0 wks) and last (Time=7 weeks) disease assessments are presented. At all disease assessments, there were no obvious signs of phyto-toxicity associated with the treatments.

Figure 12:
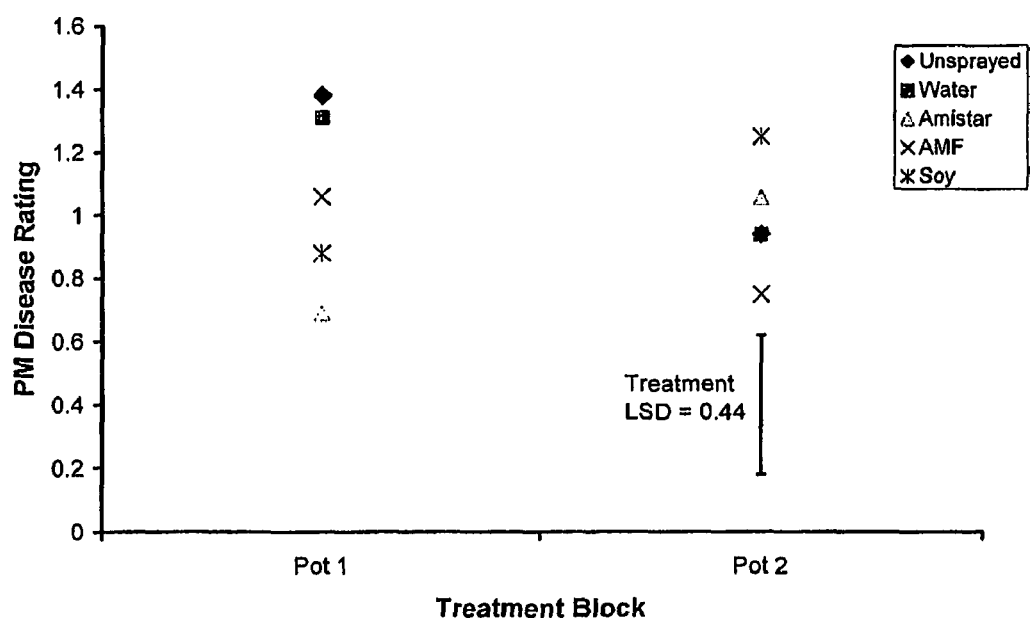
FIG. 12 shows the PM disease severity on 'Endeavour' wheat plants from Trial 6 at Time=0 weeks, i.e. prior to any treatment application. The LSD bar applies to within-column comparisons only, owing to the hierarchical nature of the nested design.
Figure 13:
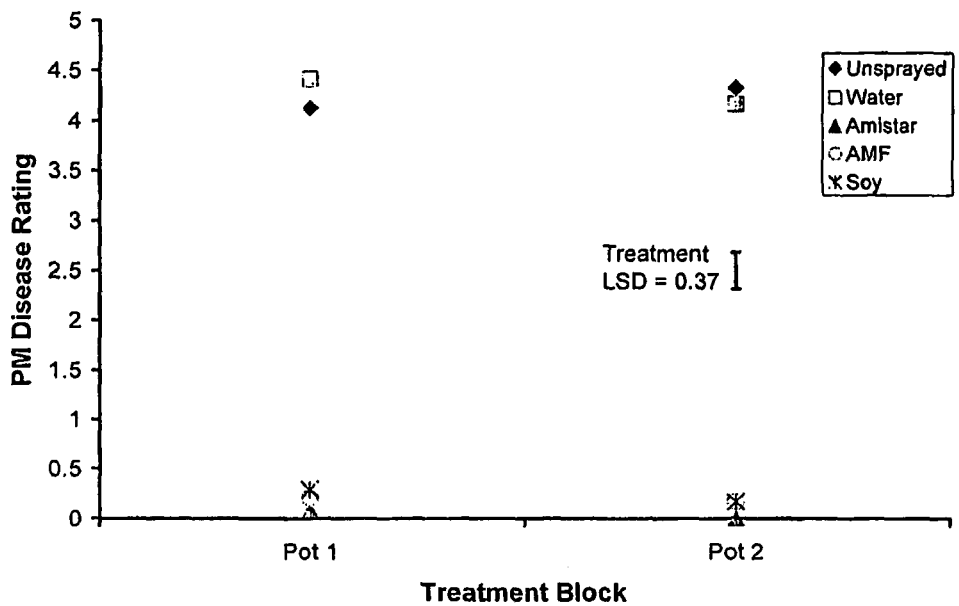
FIG. 13 shows the PM disease severity on 'Endeavour' wheat plants from Trial 6 at Time=7 weeks, i.e. after 7 weeks of treatment application. The LSD bar applies to within-column comparisons only, owing to the hierarchical nature of the nested design.

At 0 weeks, there are no consistent treatment differences evident (FIG. 12), but by 7 weeks, "Amistar", "AMF" and "Soy" all provided significantly greater control of PM than "Unsprayed" and "Water" treated controls (FIG. 13).

Trial 7—Materials and Methods

Materials and methods were the same as for Trials 2 and 3, except that 'Delica' squash plants were allowed to develop natural infection, rather than having their first true leaf artificially inoculated. Six spray applications were made at 7-day intervals with approximately 1% of the leaf area naturally infected with PM at the time of the first treatment application.

Disease severity on true leaves 1-8 was ranked fortnightly using the scale in Table 1 and qualitative assessments of leaf health/condition were made at the same time using the arbitrary scale described in Table 4.

Data were analysed as a repeated measures design (RMD) to determine the treatment effect on disease severity over time. Treatment differences at 6 weeks only were also assessed as a randomised block design (RBD), by analysis of variance (ANOVA), with means separation by Fisher's Least Significant Difference (LSD) ($P<0.05$), using SAS software, version 8.01 TS (SAS Institute, Cary, N.C.).

Trial 7—Treatments

The treatments used are summarised in Table 26

TABLE 26

Trial 7 treatments

| Treatment | Code |
|---|---|
| 1) AMF (7 g/L) + DATEM (4 g/L) emulsifier (an example of a diacetyl tartaric acid ester emulsifier) + Grindox 122 ™ (1 g/L) antioxidant | [AMF + Dat + 122] |
| 2) AMF (7 g/L) + Grindsted Citrem N12 Veg ™ (4 g/L) emulsifier (an example of a citric acid ester of monoglycerides emulsifier) + Grindox 122 ™ antioxidant | [AMF + Citrem + 122] |
| 3) AMF (7 g/L) + Grindsted PGE 20 Veg ™ (4 g/L) emulsifier (an example of a polyglycerol ester of fatty acids emulsifier) + Grindox 122 ™ antioxidant | [AMF + PGE + 122] |
| 4) AMF (7 g/L) + Grindsted PGPR 90 ™ (4 g/L) emulsifier (an example of a polyglycerol polyricinoleate emulsifier) + Grindox 122 ™ antioxidant | [AMF + PGPR + 122] |
| 5) AMF (7 g/L) + lecithin (4 g/L) emulsifier (an example of a lecithin emulsifier) + Grindox 122 ™ antioxidant | [AMF + Lecit + 122] |
| 6) AMF (7 g/L) + DATEM (4 g/L) emulsifier + Grindox AP kosher ™ (1 g/L) antioxidant (an example of an ascorbyl palmitate antioxidant) | [AMF + Dat + AP] |
| 7) AMF (7 g/L) + DATEM (4 g/L) emulsifier + Grindox TOCO70 ™ (1 g/L) antioxidant (an example of a tocopherol antioxidant) | [AMF + Dat + Toco] |
| 8) AMF (7 g/L) + DATEM (4 g/L) emulsifier + Grindox 204 ™ (1 g/L) antioxidant (an example of a tertiary butylhydroquinone (TBHQ) antioxidant) | [AMF + Dat + 204] |

TABLE 26-continued

Trial 7 treatments

| Treatment | Code |
|---|---|
| 9) AMF (7 g/L) + Grindsted CSL P 80 ™ (4 g/L) emulsifier (an example of a calcium stearoyl lactylate emulsifier) + Grindox 122 ™ antioxidant | [AMF + CSL + 122] |
| 10) Water | [H2O] |

All emulsions were prepared 1 day in advance by dissolving antioxidant in molten AMF (>40 C) followed by addition of emulsifier and hot water (70° C.), and blending for 1-2 mins, until a stable emulsion was formed.

Treatments were sourced as follows:

AMF (NZMP (NZ) Ltd); all Grinsted emulsifiers, Grindox antioxidants and DATEM Panodan™ AL 10 emulsifier (Danisco Ltd, Brabrand, Denmark); and lecithin (Hawkins Watts Ltd, Auckland, NZ).

Trial 7—Results—Randomised Block Design

Figure 14:
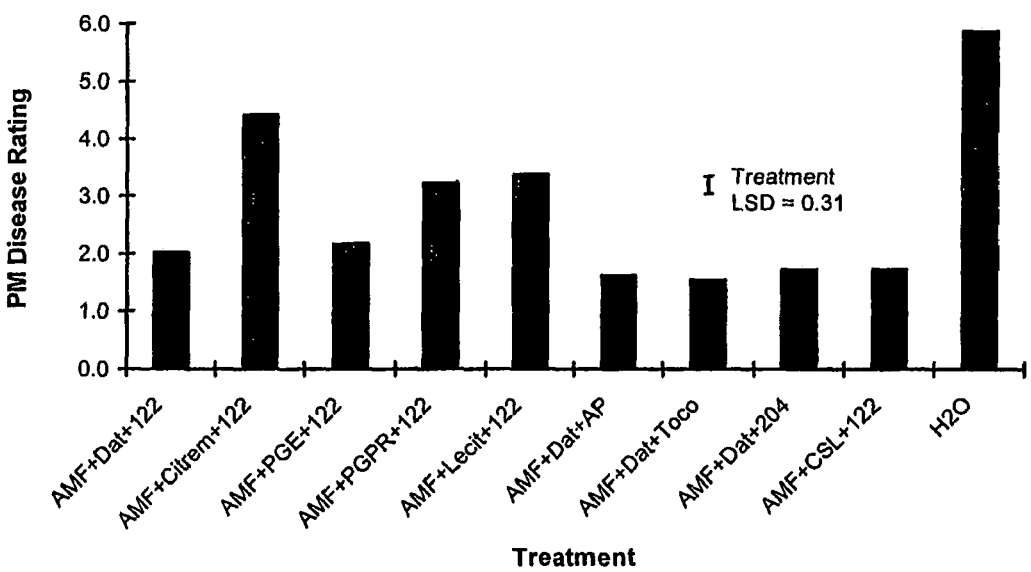
FIG. 14 shows the effects of the Trial 7 treatment application on PM disease severity on 'Delica' squash leaves, after 6 weeks of treatment application.

FIG. 14 shows the effects of Table 26 treatments on PM disease severity on 'Delica' squash leaves, after 6 weeks of treatment application.

The best treatments in order of efficaciousness were "AMF+Dat+Toco", "AMF+Dat+AP", "AMF+Dat+204", "AMF+CSL+122", "AMF+Dat+122" and "AMF+PGE+122" which limited PM severity to <5% of the leaf surface area, and performed significantly better than "AMF+PGPR+122" and "AMF+Lecit+122" which were in turn significantly more effective than "AMF+Citrem+122". "Water" treated plants had significantly more infections than all other treatments.

All of the treatments reduced PM infection relative to the water control, but they had variable effects on plant health (Table 27).

TABLE 27

Leaf health ratings of 'Delica' squash leaves after 6 weeks of treatment application

| | Treatment Code | Leaf Health Rating |
|---|---|---|
| 1) | AMF + Dat + 122 | E |
| 2) | AMF + Citrem + 122 | D |
| 3) | AMF + PGE + 122 | C |
| 4) | AMF + PGPR + 122 | E |
| 5) | AMF + Lecit + 122 | E |
| 6) | AMF + Dat + AP | D |
| 7) | AMF + Dat + Toco | E |
| 8) | AMF + Dat + 204 | E |
| 9) | AMF + CSL + 122 | C |
| 10) | H2O | G |

Trial 7—Results—Repeated Measures Design

At the start of the experiment there were no significant differences in the level of natural infection between any of the treatments (p=0.9379). With assessment of treatment effect over time (0, 2, 4 and 6 week data), highly significant treatment differences in the PM disease ratings were detectable after just 2 weeks of treatment application (p<0.0001 and Table 28). Natural infections increased significantly over time up until 4 weeks for all treatments. After this time, PM disease ratings remained the same over time or decreased, due to elimination of infections in the latter case, for all treatments except for "H2O" where disease severity continued to increase significantly until the end of the experiment.

TABLE 28

The effects of Trial 7 treatments on PM disease severity on naturally-infected 'Delica' squash leaves over time.

| | PM Disease Rating | | | |
|---|---|---|---|---|
| Treatment | 0 wks | 2 wks | 4 wks | 6 wks |
| AMF + Dat + 122 | 0.97 | 1.43 | 2.08 | 2.04 |
| AMF + Citrem + 122 | 0.89 | 3.70 | 4.55 | 4.43 |
| AMF + PGE + 122 | 0.83 | 1.58 | 2.28 | 2.19 |
| AMF + PGPR + 122 | 0.88 | 2.38 | 3.30 | 3.24 |
| AMF + Lecit + 122 | 0.89 | 2.08 | 3.20 | 3.40 |
| AMF + Dat + AP | 0.88 | 1.05 | 1.78 | 1.64 |
| AMF + Dat + Toco | 0.90 | 1.08 | 1.56 | 1.56 |
| AMF + Dat + 204 | 0.98 | 1.30 | 1.68 | 1.74 |
| AMF + CSL + 122 | 0.83 | 1.18 | 1.63 | 1.75 |
| H2O | 0.80 | 4.22 | 5.49 | 5.88 |

Time LSD = 0.28

Trial 8—Materials and Methods

Mature rose plants of the PM-susceptible cultivar 'Sahara' were pruned to a height of approximately 40 cm and potted into 20 cm diam. plastic pots with Dalton's potting mix. Plants were maintained in a controlled environment (CE) room set at a constant temperature of 20° C. and a 16 h photoperiod. Pots were hand-watered with tap water every two to three days. The plants were left for three weeks to establish, form new leaf growth, and infect naturally with PM before commencement of the trial. Roses buds and flowers were removed throughout the course of the trial.

There were five treatment applications at weekly intervals. All treatments were applied using hand-held mister bottles to the adaxial and abaxial leaf surfaces until runoff to ensure full coverage. There were six replicates (pots) per treatment. The pots were randomised within blocks on a single bench within the CE room, with one replicate plant from each treatment in each block.

Disease assessments were carried out immediately prior to each spray application and one week after the last spray. Assessments of PM were based on the disease rating scale in Table 1, except that assessments were not carried out on individual leaves as in Trials 1-3 and 7, because roses have relatively rapid growth and turnover of leaves. Rather, the disease rating was given as an overall average for the mature portion of the plant, excluding all the fresh unexpanded juvenile leaves. Data from the final assessment were analysed as a randomised block design (RBD), by analysis of variance (ANOVA), with means separation by Fisher's Least Significant Difference (LSD) (P<0.05), using SAS software, version 8.01 TS (SAS Institute, Cary, N.C.).

Trial 8—Treatments
There were five treatments (Table 29):

TABLE 29

Trial 8 treatments

| Treatment | Code |
|---|---|
| 1) Unsprayed control | [Unsprayed] |
| 2) Distilled water control | [Water] |
| 3) Fungicide - Supershield ™ (Yates, NZ) (10 ml/L) | [Supershield] |
| 4) AMF (7 g/L) + DATEM (4 g/L) emulsifier + Grindox 122 ™ (1 g/L) antioxidant | [AMF] |
| 5) Soy (20 ml/L) + DATEM (4 g/L) emulsifier + Grindox 122 ™ (1 g/L) antioxidant | [Soy] |

Trial 8—Results

Figure 15:
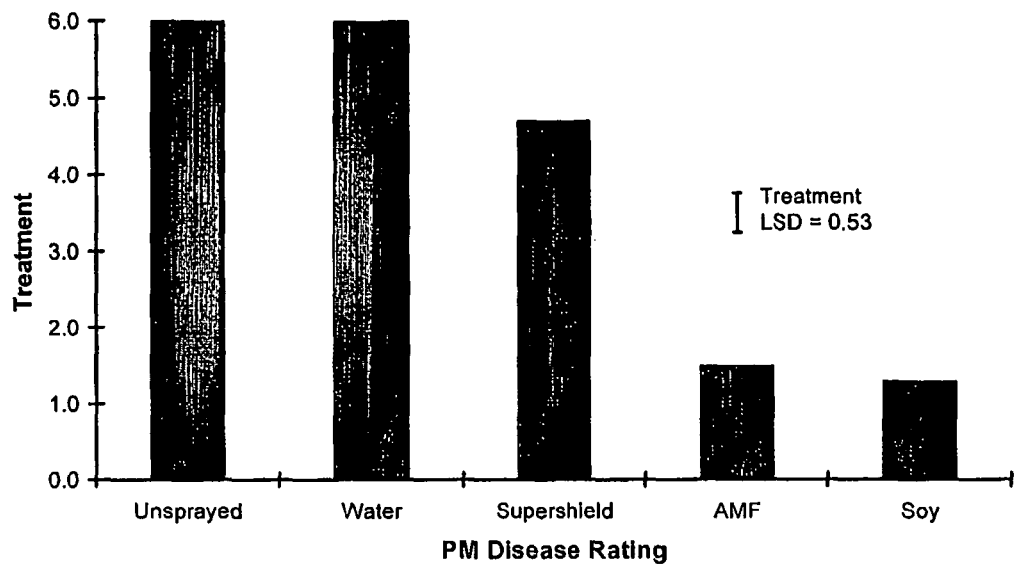
FIG. 15 shows effects of Trial 8 treatment application on PM disease severity on 'Sahara' rose bushes, after 6 weeks of treatment application.

FIG. 15 shows that "Soy" and "AMF" were the best treatments providing significantly better PM disease control than "Supershield" fungicide, which in turn had significantly reduced disease relative to the "Water" and "Unsprayed" treatments.

Trial 9—Materials and Methods

'Royal Gala' apple seedlings with approximately 8 true leaves were potted into 10 cm diam. plastic pots using Butlers' potting mix, and were maintained in a controlled environment (CE) room set at a constant temperature of 20° C. and a 16 h photoperiod. Pots were hand-watered with tap water every two to three days. Plants were already showing initial signs of natural PM infection (<1% of the leaf surface area infected) at the time of the first treatment application.

All treatments were applied weekly over the course of 7 weeks to adaxial and abaxial leaf surfaces until runoff to ensure full coverage. There were eight replicates (pots) per treatment. One replicate from each treatment was randomised with, each block on a single bench within the CE room.

Leaf assessments were carried out immediately prior to each spray application and one week after the last spray. Assessments of PM disease severity were based on the disease rating scale in Table 1. At each assessment, the number of leaves on each apple seedling was determined, excluding all the fresh unexpanded juvenile leaves, and ratings were given for every individual leaf and the mean leaf disease rating was calculated for each plant. Disease incidence was determined as the percentage of leaves expressing PM out of the total number of leaves on each plant At the conclusion of the experiment, two harvest parameters were measured. The plants were excised at ground level, and plant height (cm) was measured from ground level to the tip of the stem. Excised plants were oven-dried at 80° C. and dry weights of the above ground plant parts were determined.

PM disease severity ratings and disease incidence from the final assessment, and harvest parameters were each analysed using a randomised block design (RBD), by analysis of variance (ANOVA), with means separation by Fisher's Least Significant Difference (LSD) (P<0.05), using SAS software, version 8.01 TS (SAS Institute, Cary, N.C.).

Trial 9—Treatments
There were five treatments (Table 30):

TABLE 30

Trial 9 treatments

| Treatment | Code |
|---|---|
| 1) Unsprayed control | [Unsprayed] |
| 2) Distilled water control | [Water] |

TABLE 30-continued

Trial 9 treatments

| Treatment | Code |
|---|---|
| 3) Fungicide - Kumulus ® DF (BASF, Germany) (1 g/L) | [Kumulus] |
| 4) AMF (7 g/L) + DATEM (4 g/L) emulsifier + Grindox 122 ™ (1 g/L) antioxidant | [AMF] |
| 5) Soy (20 ml/L) + DATEM (4 g/L) emulsifier + Grindox 122 ™ (1 g/L) antioxidant | [Soy] |

Trial 9—Results

Figure 16:
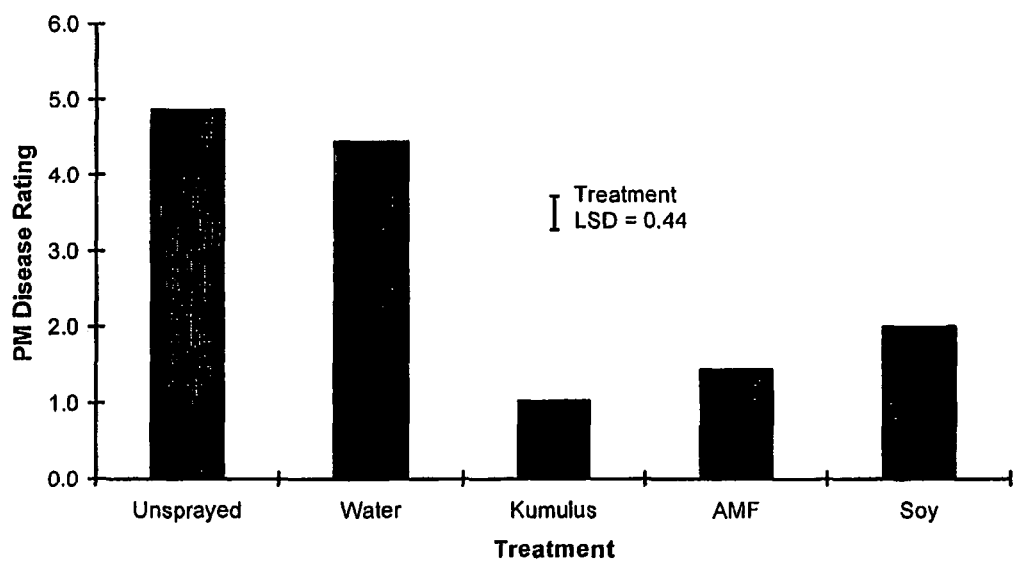
FIG. 16 shows the effects of Trial 9 treatment application on PM disease severity on leaves of 'Royal Gala' apple seedlings, after 7 weeks of treatment application.

The lowest disease severities were found in the "Kumulus" and "AMF" treatments (FIG. 16). Disease control efficacy was the greatest in these two treatments followed by "Soy" which was significantly better than "H2O and "Unsprayed" treatments (FIG. 16).

Figure 17:
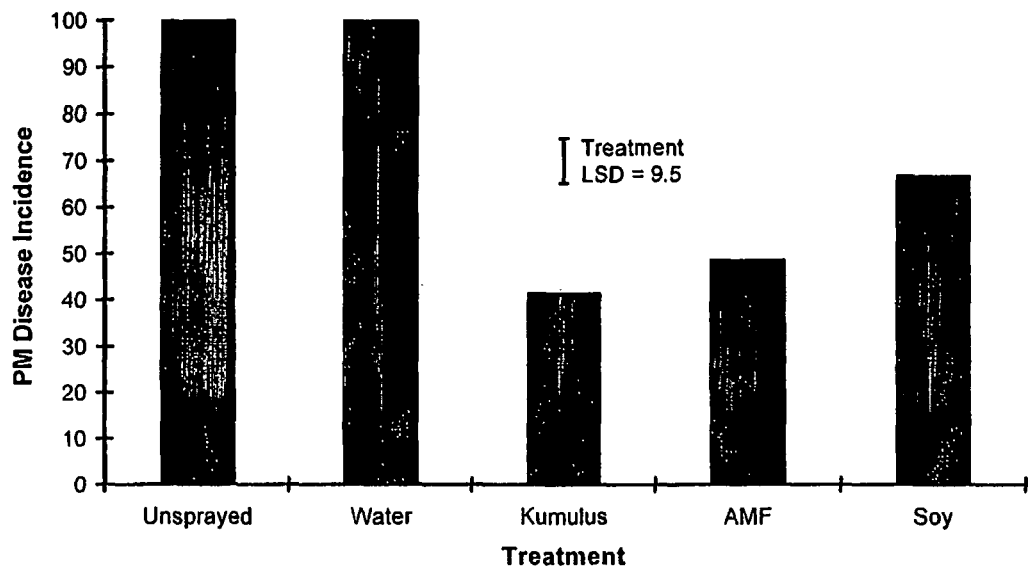
FIG. 17 shows the effects of Trial 9 treatment application on PM disease incidence on leaves of 'Royal Gala' apple seedlings, after 7 weeks of treatment application.

Disease incidence treatment rankings shown in FIG. 17 were the same as the disease severity rankings in FIG. 16, i.e. "Kumulus" and "AMF" treatments resulted in the lowest disease incidence, followed by "Soy" which in turn had significantly lower disease incidence than the "H2O and "Unsprayed" treatments (FIG. 17).

Figure 18:
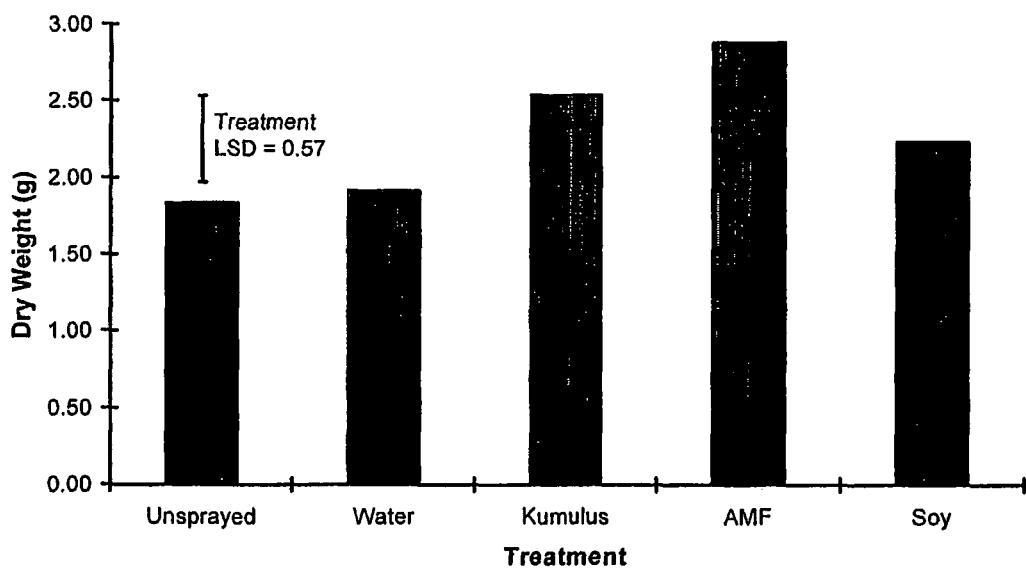
FIG. 18 shows the effects of Trial 9 treatment application on 'Royal Gala' apple seedling dry weights, after 7 weeks of treatment application.

FIG. 18 shows that dry weights were greatest in the "AMF" treatment, intermediate in the "Kumulus" and "Soy" treatments and lowest in the "H2O" and "Unsprayed" treatments.

Figure 19:
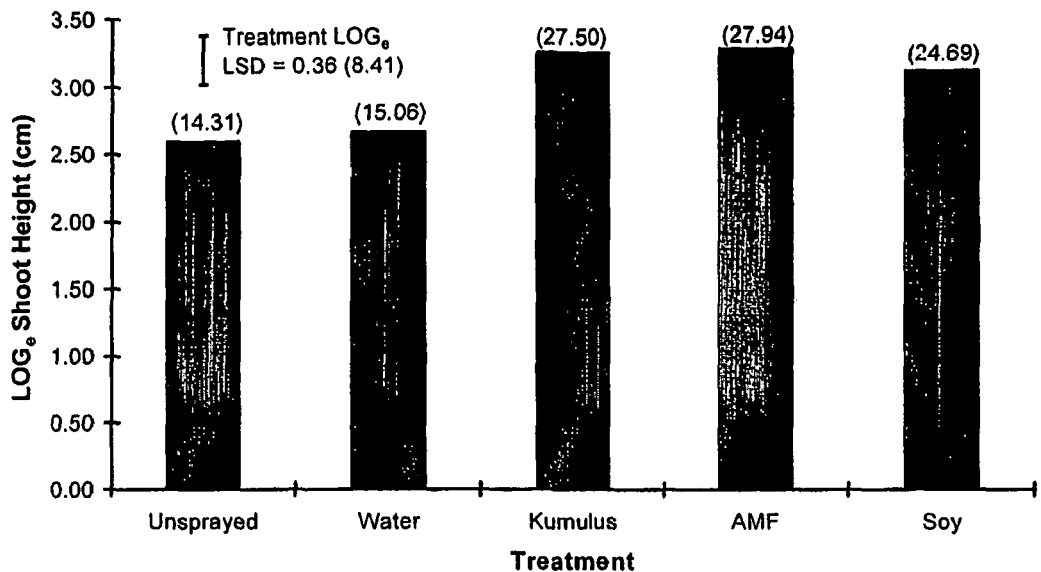
FIG. 19 shows the effects of Trial 9 treatment application on 'Royal Gala' apple seedling heights, after 7 weeks of treatment application. The data required a loge transformation to satisfy the assumptions required for ANOVA (normal distribution and homogeneity of variances). The corresponding untransformed values for each data point are given in parentheses.
Figure 20:
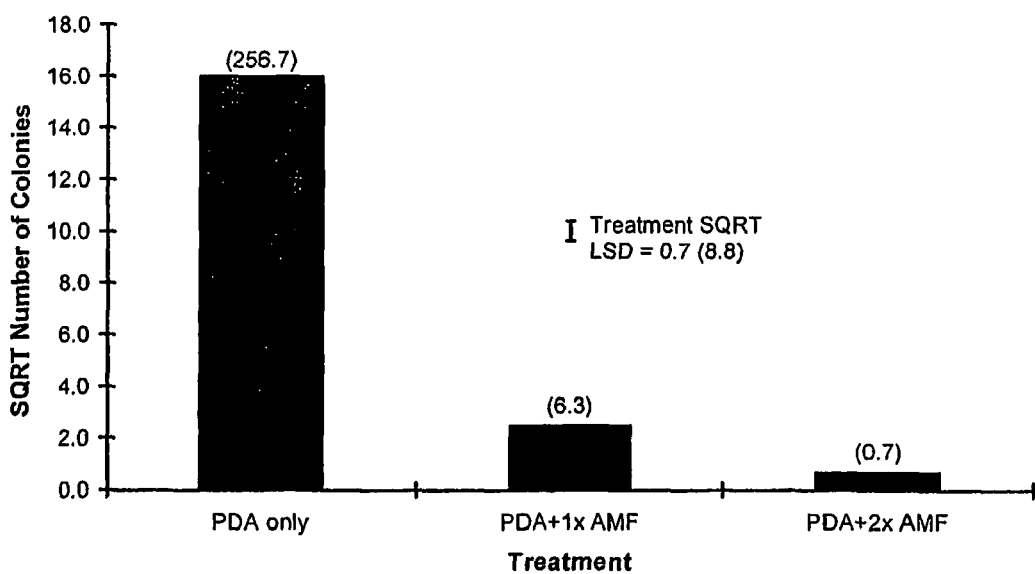
FIG. 20 shows the effects of Trial 10 media amendment on *Mycosphaerella fijiensis* colony number. ANOVA analysis necessitated a square root (SQRT) data transformation. The corresponding untransformed values for each data point are given in parentheses.
Figure 21:
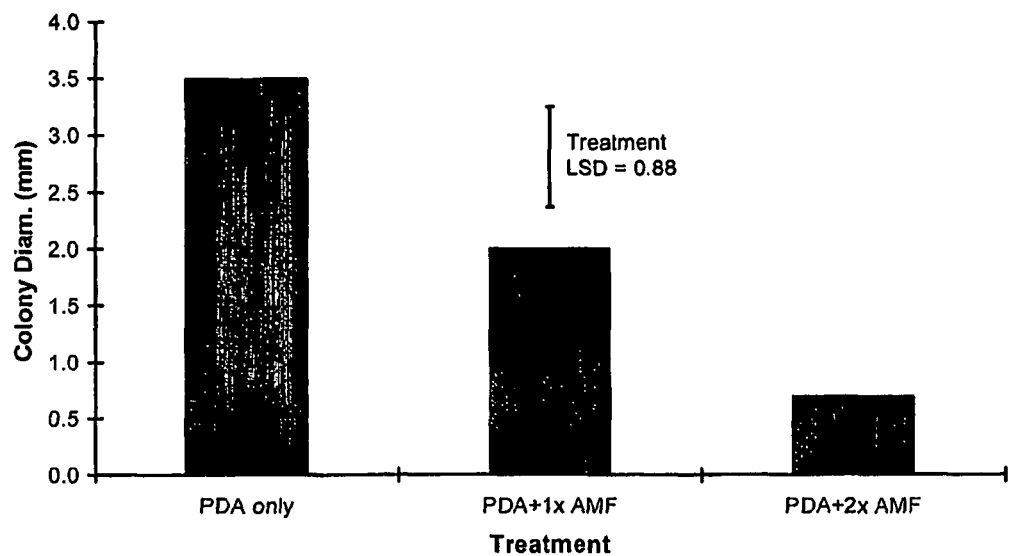
FIG. 21 shows the effects of Trial 10 media amendment on *Mycosphaerella fijiensis* colony diameter.

Shoot height data in FIG. 19 required a loge transformation to satisfy the assumptions required for ANOVA (normal distribution and homogeneity of variances). The corresponding untransformed values for each data point are given in parentheses. "Unsprayed" and "H2O" treated plants were significantly more stunted than those in the "Soy", "Kumulus" and "AMF" treatments (FIG. 19).

Trial 10—Materials and Methods

Suspensions of a mixture of spores and mycelial fragments of Strain 298 of *Mycosphaerella fijiensis* were spread over the following growth media.

1) Potato Dextrose Agar (PDA) unamended
2) PDA amended with single strength AMF (10 ml of x10 concentration/100 ml medium).
3) PDA amended with double strength AMF (20 ml of x10 concentration/100 ml medium).

There were three replicate plates of each concentration.

Plates were inoculated, incubated at 23 to 24° C. with a 12 hour photoperiod and assessed after 25 days growth.

Trial 10—Results

ANOVA analysis of the colony number data in FIG. 20 necessitated a square root (SQRT) data transformation. The corresponding untransformed values for each data point are given in parentheses. Single strength AMF significantly reduced the number of colonies growing on PDA and doubling the strength of AMF caused a further significant reduction in colony number (FIG. 20).

Single strength AMF significantly reduced the mean colony diameter on PDA and doubling the strength of AMF caused a further significant reduction in colony diameter (FIG. 21).

Trial 11—Materials and Methods

Mature grapevines (*Vitis vinifera*) cv. Chardonnay were allowed to infect naturally. There were six treatments as shown in Table 31. Nine sprays were applied between capfall and harvest as detailed in Table 32, at an application rate of 500 L/ha during capfall and thereafter at 800 L/ha. The milk fat and soy fungicides were prepared as emulsifiable concentrates, diluted 25-fold with water immediately prior to use.

Percentage of total fruit crop infected by *Botrytis cinerea* and powdery mildew was calculated as the product of disease incidence (percentage of bunches infected) and mean disease severity (percentage of bunch area covered by disease), using a sample size of 50 bunches per plot. PM infections on fruit were assessed at veraison. *B. cinerea* infections on fruit, yield (kg fruit/m) and percent canopy leaf burn were assessed at harvest. The experiment was analysed as a randomised block design with 5 blocks and one plot of two vines per treatment per block. The outermost 1.5 m of each plot was disregarded when sampling bunches. ANOVA and means separation by LSD (P<0.05) were performed using SAS software, version 8.02 (SAS Institute, Cary, N.C.).

Trial 11—Treatments

TABLE 31

Trial 11 treatments.

| Treatment | Abbreviated Treatment Code |
|---|---|
| Unsprayed (nil fungicides) | [Unsprayed] |
| Powdery mildew fungicides only (Kumulus ® DF, and Topas ®) | [PM Fung Only] |
| Standard fungicide spray programme for export quality grapes (Euparen ® Multi, Scala ®, Switch ®, Captan WG, Teldor ®, Topas ® 200EW, and Kumulus ® DF) | [Std Fung] |
| AMF (7 g/L) + DATEM (4 g/L) emulsifier + Grindox 122 ™ (1 g/L) antioxidant | [AMF Only] |
| Soy (20 ml/L) + DATEM (4 g/L) emulsifier + Grindox 122 ™ (1 g/L) antioxidant | [Soy Only] |
| AMF early and mid season, then fungicide (Scala ® and Captan WG) late season | [AMF/Late Fung] |

The fungicide Captan WG is produced by Crop Care Australasia (Brisbane, Australia); Scala®, Euparen® Multi, and Teldor® by Bayer AG, Germany; Switch®, and Topas® 200EW by Syngenta (Basel, Switzerland); and Kumulus® DF by BASF, Germany.

TABLE 33

Effect of Trial 11 treatments on the percentage of total fruit crop infected by PM, assessed at veraison.

| Treatment Code | $Log_e$ Mean % Fruit Crop Infected by PM | Means Separation by LSD* |
|---|---|---|
| Unsprayed | 1.35 (4.60) | A |
| AMF Only | −0.42 (0.70) | AB |
| Std Fung | −2.81 (0.02) | BC |
| PM Fung Only | −3.11 (0.02) | C |
| AMF/Late Fung | −3.55 (0.01) | C |
| Soy Only | −3.91 (0.01) | C |

LSD = 2.62 (2.58)
*Means separated by different letters are significantly different.

The most effective treatments in preventing PM were "Soy", "AMF/Late Fung" and "PM Fung Only". Use AMF during the early/mid season and standard fungicides late season provided better disease control than if AMF or standard fungicides were used on their own throughout the whole season (Table 33).

Figure 22:
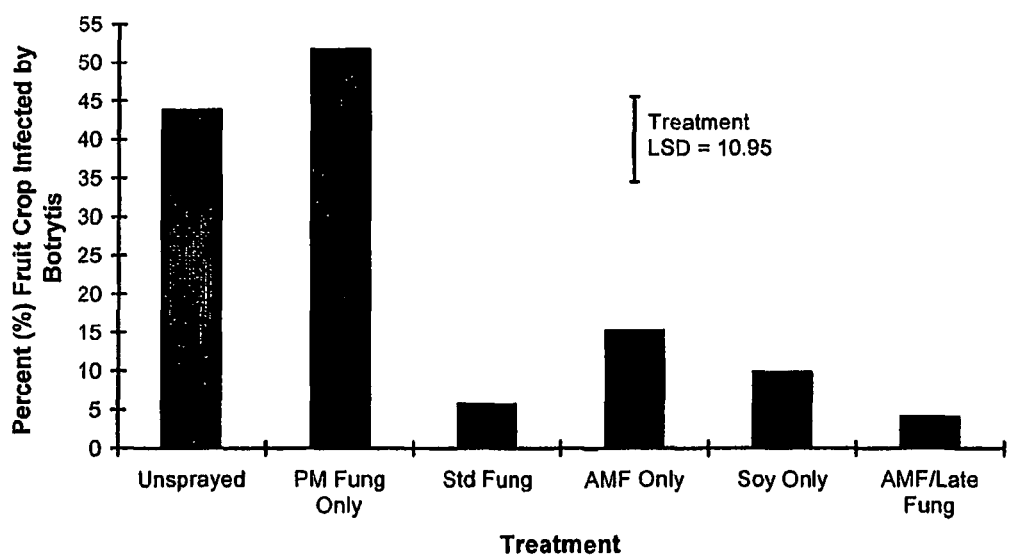
FIG. 22 shows the effect of Trial 11 treatments on the percentage of fruit crop of 'Chardonnay' grapes infected by *Botrytis cinerea*, assessed after a 4-month spray programme.

"AMF/Late Fung" provided significantly better Botrytis control than "AMF only", which in turn gave significantly better control than "Unsprayed" and "PM Fung Only" (FIG. 22). Botrytis control efficacy on the "Std Fung" and "NP2 only" treatments was intermediate between "AMF/Late Fung" and "AMF Only" (FIG. 22).

Figure 23:
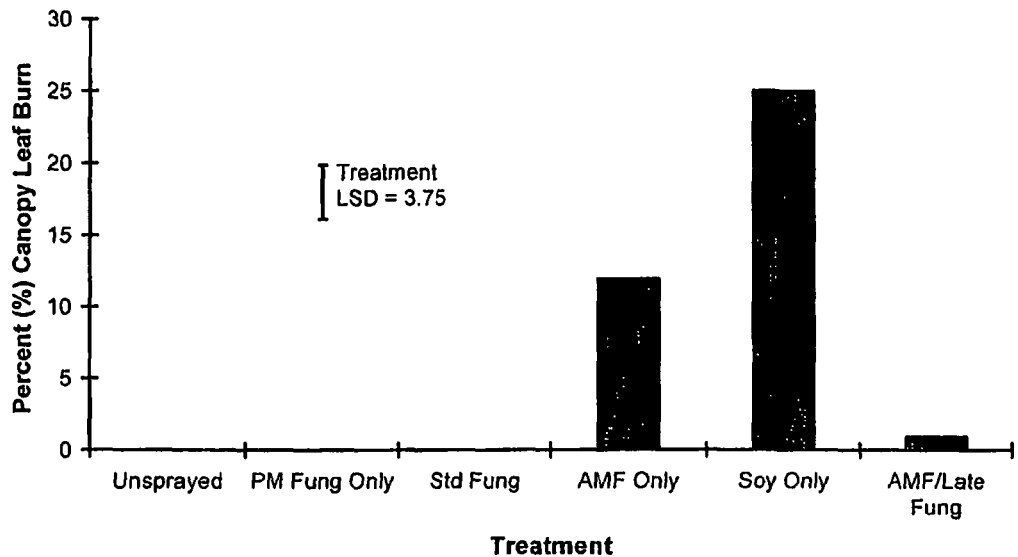
FIG. 23 shows the effect of Trial 11 treatments on percentage leaf burn in a 'Chardonnay' grapevine canopy, assessed after a 4-month spray programme.

Use of either Soy or AMF throughout the entire grape season caused significant phyto-toxicity, but this problem was eliminated by restricting AMF application to the early/mid season and using standard fungicides late season (FIG. 23).

Figure 24:
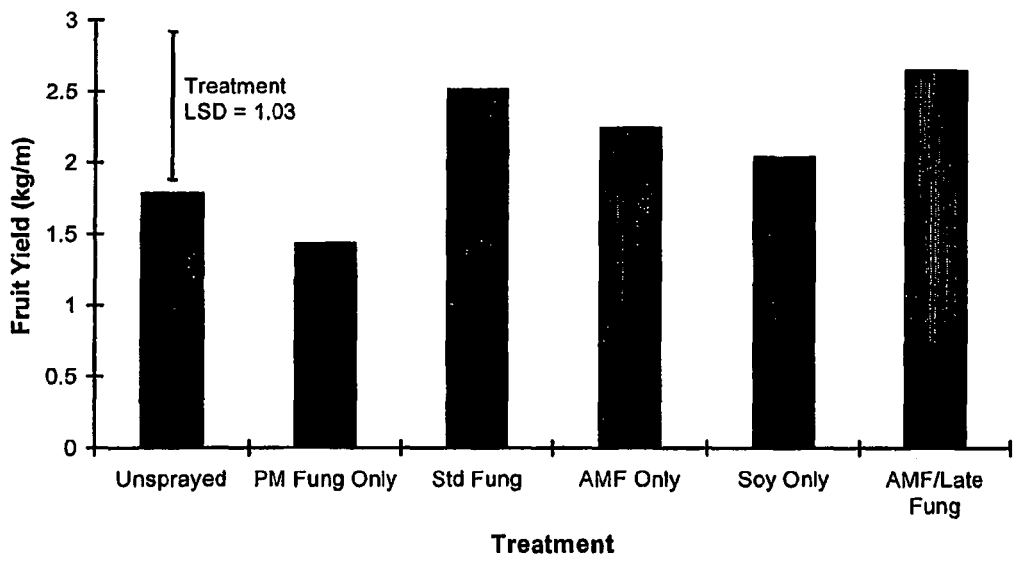
FIG. 24 shows the total 'Chardonnay' grape berry yield (kg/m) in Trial 11.

Crop yield were highest in the "AMF/Late Fung" treatment, followed by "Std Fung" (FIG. 24). The yields of these 2 treatments were significantly greater than the "PM Fung

TABLE 32

Trial 11 treatment application schedule.

| | Vine Phenology At Time of Spray Application (early/mid/late season) | | | | | | | | |
|---|---|---|---|---|---|---|---|---|---|
| Treatment Code | 5% capfall (early) | 90% capfall (early) | Post bloom (early) | Berries pea size (early) | Pre-bunch closure (mid) | Post bunch closure (mid) | Veraison (late) | 4 wk pre-vintage (late) | 2 wk pre-vintage (late) |
| Unsprayed | — | — | — | — | — | — | — | — | — |
| PM Fung Only | Kumulus 30 g/10 L | Kumulus 30 g/10 L | Topas 200EW 1.25 ml/10 L | Kumulus 30 g/10 L | Kumulus 30 g/10 L | Kumulus 30 g/10 L | — | — | — |
| Std Fung | Euparen Multi 10 g/10 L | Switch 8 g/10 L | Topas 200EW 1.25 ml/10 L Kumulus 30 g/10 L | Captan 12.5 g/10 L Kumulus 30 g/10 L | Teldor 7.5 ml/10 L Kumulus 30 g/10 L | Captan 12.5 g/10 L Kumulus 30 g/10 L | Scala 20 ml/10 L | Captan 12.5 g/10 L | — |
| AMF Only | All applications: AMF (7 g/L) + Datem (4 g/L) + Grindox 122 (1 g/L) | | | | | | | | |
| Soy Only | All applications: Soy (20 ml/L) + Datem (4 g/L) + Grindox 122 (1 g/L) | | | | | | | | |
| AMF/Late Fung | All applications: AMF (7 g/L) + Datem (4 g/L) + Grindox 122 (1 g/L) | | | | | | Scala 20 ml/10 L | Captan 12.5 g/10 L | — |

Trial 11—Results

Table 33 shows the effects of Trial 11 treatments on the percentage of total fruit crop infected by PM, assessed at veraison. Data required a $log_e$ transformation to satisfy the assumptions of ANOVA (normal distribution and homogeneity of variances). Corresponding untransformed values are provided in parentheses.

Only" treatment, with all other treatment yields intermediate between these upper and lower values (FIG. 24).

INDUSTRIAL APPLICATION

The compositions and methods of the invention have applications in the management (prevention and control) of fungal growth in commercial and small scale crop production.

The compositions of the invention may be applied in any suitable form but are preferably sprayable.

The compositions and methods of the invention allow a reduction in the use of systemic fungicides.

In one embodiment the compositions and methods of the invention are useful to control Powdery Mildew (PM), Botrytis diseases and Sour Rots in grapes.

In one embodiment the compositions and methods of the invention are useful to control PM in field and glasshouse-grown cucurbits (squash, pumpkins, zucchini, melons, cucumbers).

In one embodiment the compositions and methods of the invention are useful to control PM on apple seedlings in nurseries.

In one embodiment the compositions and methods of the invention are useful to control powdery mildew on roses.

In one embodiment the compositions and methods of the invention are useful to control *Botrytis* on other crops, for example tomatoes and ornamental varieties.

Those persons skilled in the art will understand that the above description is provided by way of illustration only and that the invention is not limited thereto.

REFERENCES

1. Bettiol, W. 1999: Effectiveness of cow's milk against zucchini squash powdery mildew (*Sphaerotheca fuliginea*) in greenhouse conditions. Crop Protection 18:489-492
2. Crisp, P., and D. Bruer. 2001. Organic control of powdery mildew without sulfur. Australian Grapegrower and Winemaker 452:22
3. Kabara, J. 1984. Antimicrobial agents derived from fatty acids. Journal of the American Oil Chemists' Society 61: 397-403
4. Kabara, J. 1978. Fatty acids and derivatives as antimicrobial agents—a review. American Oil Chemists' Society Monograph 5:1-14
5. Nieman, C. 1954. Influence of trace amounts of fatty acids on the growth of microorganisms. Bacteriological Reviews 18: 147-163
6. Cheah, L. H. and Cox, J. K. 1995. Screening of plant extracts for control of powdery mildew in squash. Proceedings of the 48th NZ Plant Protection Conference: 340-342
7. McGrath, M. T. and Shishkiff, N. 1999. Evaluation of biocompatible products for anaging cucurbit powdery mildew. Crop Protection 18: 471-478
8. Ko, W. H. et al. 2003. Effects of sunflower oil on tomato powdery mildew caused by Oidium neolycopersici. Journal of Phytopathology 151(3): 144-148
9. Spencer, D. M. 1977: Standardized methods for the evaluation of fungicides to control cucumber powdery mildew. Pages 455-464 in: Crop Protection Agents—Their Biological Evaluation. N. R. McFarlane, ed. Academic Press, London.
10. Wilson, C. et al. 1997. Rapid evaluation of plant extracts and essential oils for antifungal activity against *Botrytis cinerea*. Plant Disease 81: 204-210
11. James, W. C. 1971: An illustrated series of assessment keys for plant diseases, their preparation and usage. Canadian Plant Disease Survey 51: 39-65

What we claim is:

1. A method of preventing or controlling a fungal infection in plants comprising applying to a plant in need thereof an effective amount of a composition comprising:
    (a) isolated anhydrous milk fat (AMF), and
    (b) one or more of an agriculturally acceptable carrier, an emulsifier and an antioxidant
wherein the composition is substantially free of milk proteins and milk carbohydrates.

2. A method of preventing or controlling a fungal infection in plants comprising applying to a plant in need thereof an effective amount of a composition consisting essentially of:
    (a) anhydrous milk fat (AMF), and
    (b) one or more of an agriculturally acceptable carrier, an emulsifier and an antioxidant
wherein the composition is substantially free of milk proteins and milk carbohydrates.

3. The method as claimed in claim 2 wherein the AMF is at least about 1-30 g/L.

4. The method as claimed in claim 2 wherein the emulsifier is at least about 0.5-10 g/L.

5. The method as claimed in claim 2 wherein the antioxidant is at least about 0.1-5.0 g/L.

6. The method as claimed in claim 2 wherein the AMF is from about 1 g/L to about 30 g/L, the emulsifier is from about 1 g/L to about 10 g/L, the antioxidant is about 0.1 g/L to about 5 g/L.

7. The method as claimed in claim 2 wherein the AMF is from about 5 g/L to about 15 g/L, the emulsifier is from about 2 g/L to about 6 g/L, the antioxidant is from about 0.5 g/L to about 1.5 g/L.

8. The method as claimed in claim 2 wherein the AMF is about 7 g/L to about 14 g/L, the emulsifier is about 4 to 5 g/L, the antioxidant is about 1 g/L.

9. The method as claimed in claim 2 wherein the composition is an aqueous composition.

10. The method as claimed in claim 2 wherein the emulsifier is selected from the group consisting of glycerin fatty acid esters; mono- and di-glycerides; distilled monoglycerides; citric acid esters of monoglycerides; diacetyl tartaric acid esters of mono- and di-glycerides; polyglycerol esters of fatty acids; polyglycerol polyricinoleate; sorbitan esters of fatty acids; sucrose esters of fatty acids; calcium stearoyl lactylates; sodium stearoyl lactylates; lecithin; enzyme digested lecithin; caseinates including sodium caseinates; gums, a xanthan gum, a xanthan gum from corn; a polysorbate 80; a composition comprising polyethylene oxide and oleic acid; a composition comprising 90% polyethylene oxide and 10% oleic acid; sodium caseinate; 93% sodium caseinate; and food grade mono- and di-glycerides derived from vegetable and animal fats but without addition of acids like tartatic acid.

11. The method as claimed in claim 2 wherein the antioxidant is one or more antioxidant agents selected from the group consisting of ascorbyl palmitate; tocopherol; alpha-tocopherol; rosemary extract; propyl gallate; tertiary butylhydroquinone; butylated hydroxyanisole; butylated hydroxytoluene; chelating agents; a composition comprising propyl gallate and food-grade citric acid monoglyceride esters; a composition comprising 20% propyl gallate and 80% food-grade citric acid monoglyceride esters; a composition comprising butylated hydroxyanisole and vegetable oil; a composition comprising 20% butylated hydroxyanisole and 80% vegetable oil; and a rosemary extract comprising about 5% phenolic diterpenes from Rosemarinus officinalis and 95% of a mixture comprising propylene glycol, mono- and di-glycerides of fatty acids, and acetic acid esters of mono- and di-glycerides of fatty acids.

12. The method as claimed in claim 2, wherein the composition is formulated as a dip, a spray or a concentrate.

13. The method as claimed in claim 2, wherein the infection is by one or more pathogens selected from powdery mildew (PM), sooty mould, Botrytis mould, grape sour bunch rot, and banana leaf spot pathogens, PM pathogens, *Sphaerotheca* pathogens, *Sphaerotheca fuliginea*, *Erysiphe* pathogens, *Erysiphe cichoracearum, Uncinula* pathogens, *Uncinula necator, Erysiphe* pathogens, *Erysiphe graminis* f. sp. *tritici, Sphaerotheca* pathogens, *Sphaerotheca pannosa* var. *rosae, Podosphaera* pathogens, *Podosphaera leucotricha,* Botrytis pathogens, *Botrytis cinerea*; sooty mould pathogens, grape sour bunch rot pathogens, downy mildew pathogens, *Plasmopara* pathogens, *Plasmopara viticola,* banana leaf spot pathogens, *Mycosphaerella* pathogens, *Mycosphaerella fijiensis, Mycosphaerella musicola,* Yellow Sigatoka, and *Mycosphaerella musae*.

14. The method as claimed in claim 2 for inhibiting germination of fungal spores.

15. The method as claimed in claim 14, wherein the fungal spores are spores of one or more of *Botrytis cinerea, Cladosporium cladosporiodes,* and *Monilinia fructicola*.

16. The method as claimed in claim 2, wherein the AMF is a substantially anhydrous composition comprising at least about 85% to about 99.9% milk fat by weight.

17. A method of preventing or controlling a fungal infection in plants comprising applying to a plant in need thereof an effective amount of a composition consisting essentially of:
(a) anhydrous milk fat,
(b) an emulsifier, and
(c) one or more of an agriculturally acceptable carrier and an antioxidant
wherein the composition is substantially free of milk proteins and milk carbohydrates.

18. A method of preventing or controlling a fungal infection in plants comprising applying to a plant in need thereof an effective amount of a composition consisting essentially of:
(a) anhydrous milk fat,
(b) an emulsifier, and
(c) water and an antioxidant
wherein the composition is substantially free of milk proteins and milk carbohydrates.

19. A method of preventing or controlling a fungal infection in plants comprising applying to a plant in need thereof an effective amount of a composition consisting of:
(a) anhydrous milk fat (AMF), and
(b) one or more of an agriculturally acceptable carrier, an emulsifier and an antioxidant.

20. A method of preventing or controlling a fungal infection by a powdery mildew or botrytis pathogen in a plant comprising the step of applying to said plant a composition consisting of:
(a) anhydrous milk fat (AMF); and
(b) one or more of an agriculturally acceptable carrier, an emulsifier and an antioxidant.

21. The method as claimed in claim 20 wherein the AMF is about 30 g/L and the emulsifier is HV40 in an amount of 4 g/L.

22. A method of preventing or controlling a fungal infection in plants comprising applying to a plant in need thereof a composition consisting essentially of:
(a) anhydrous milk fat (AMF) and one or more of soybean oil, olive oil and coconut fat, and
(b) one or more of an agriculturally acceptable carrier, an emulsifier and an antioxidant
wherein the composition is substantially free of milk proteins and milk carbohydrates.

23. The method as claimed in claim 22 wherein the coconut fat is at least about 1-30 g/L.

24. The method as claimed in claim 22 wherein the olive oil is at least about 1-30 ml/L.

25. The method as claimed in claim 22 wherein the soybean oil is at least about 1-40 ml/L.

* * * * *